United States Patent [19]
Krogh

[11] Patent Number: 5,707,348
[45] Date of Patent: Jan. 13, 1998

[54] INTRAVENOUS BANDAGE

[76] Inventor: Steve S. Krogh, 9 Sumac Dr., Mason City, Iowa 50401

[21] Appl. No.: 469,879

[22] Filed: Jun. 6, 1995

[51] Int. Cl.$^6$ .................................................. A61M 5/32
[52] U.S. Cl. .................. 602/41; 602/54; 602/57; 604/174; 604/180
[58] Field of Search ....................... 604/180, 304, 604/305, 307, 308, 174, 179; 602/41–45, 52, 54, 57, 58; 128/888, 889, DIG. 26

[56] References Cited

U.S. PATENT DOCUMENTS

| | | |
|---|---|---|
| 2,129,983 | 4/1938 | Bacon . |
| 3,323,774 | 6/1967 | Wilson . |
| 3,517,909 | 6/1970 | Santomieri . |
| 3,785,378 | 1/1974 | Stewart . |
| 4,317,473 | 3/1982 | Gaydos . |
| 4,334,530 | 6/1982 | Hassell ................................ 602/42 |
| 4,410,164 | 10/1983 | Kamen . |
| 4,413,621 | 11/1983 | McCracken et al. ................ 602/52 |
| 4,449,975 | 5/1984 | Perry . |
| 4,493,710 | 1/1985 | King et al. . |
| 4,596,560 | 6/1986 | Simpson . |
| 4,666,432 | 5/1987 | McNeish et al. . |
| 4,694,856 | 9/1987 | Leibinsohn . |
| 4,743,232 | 5/1988 | Kruger ............................. 602/52 X |
| 4,804,360 | 2/1989 | Kamen . |
| 4,917,112 | 4/1990 | Kalt ................................. 602/58 |
| 4,941,882 | 7/1990 | Ward et al. . |
| 4,976,698 | 12/1990 | Stokley . |
| 5,035,687 | 7/1991 | Sandbank . |
| 5,147,320 | 9/1992 | Reynolds et al. . |
| 5,344,415 | 9/1994 | DeBusk ............................ 604/304 |
| 5,372,589 | 12/1994 | Davis ................................ 604/180 |

FOREIGN PATENT DOCUMENTS

| | | | |
|---|---|---|---|
| 2035096 | 6/1980 | United Kingdom ............... | 604/180 |

*Primary Examiner*—Richard J. Apley
*Assistant Examiner*—Kim M. Lee
*Attorney, Agent, or Firm*—Hugh D. Jaeger

[57] ABSTRACT

An intravenous bandage for securation of an intravenous administration tube to the epidermis. A preformed bandage includes a pocket in which a bended portion of an administration tube is held in secured capture. Frangible perforations provide for timely deployment and use of various sterile members of the intravenous bandage including a member having a transparent membrane which aligns over a puncture site. One embodiment includes an umbilicus member which is incorporated for attachment of the administration tube to the epidermis. Another alternate embodiment includes a foldable clip member for frictional engagement and capture of a tube or appliance which includes an expandable shroud.

21 Claims, 33 Drawing Sheets

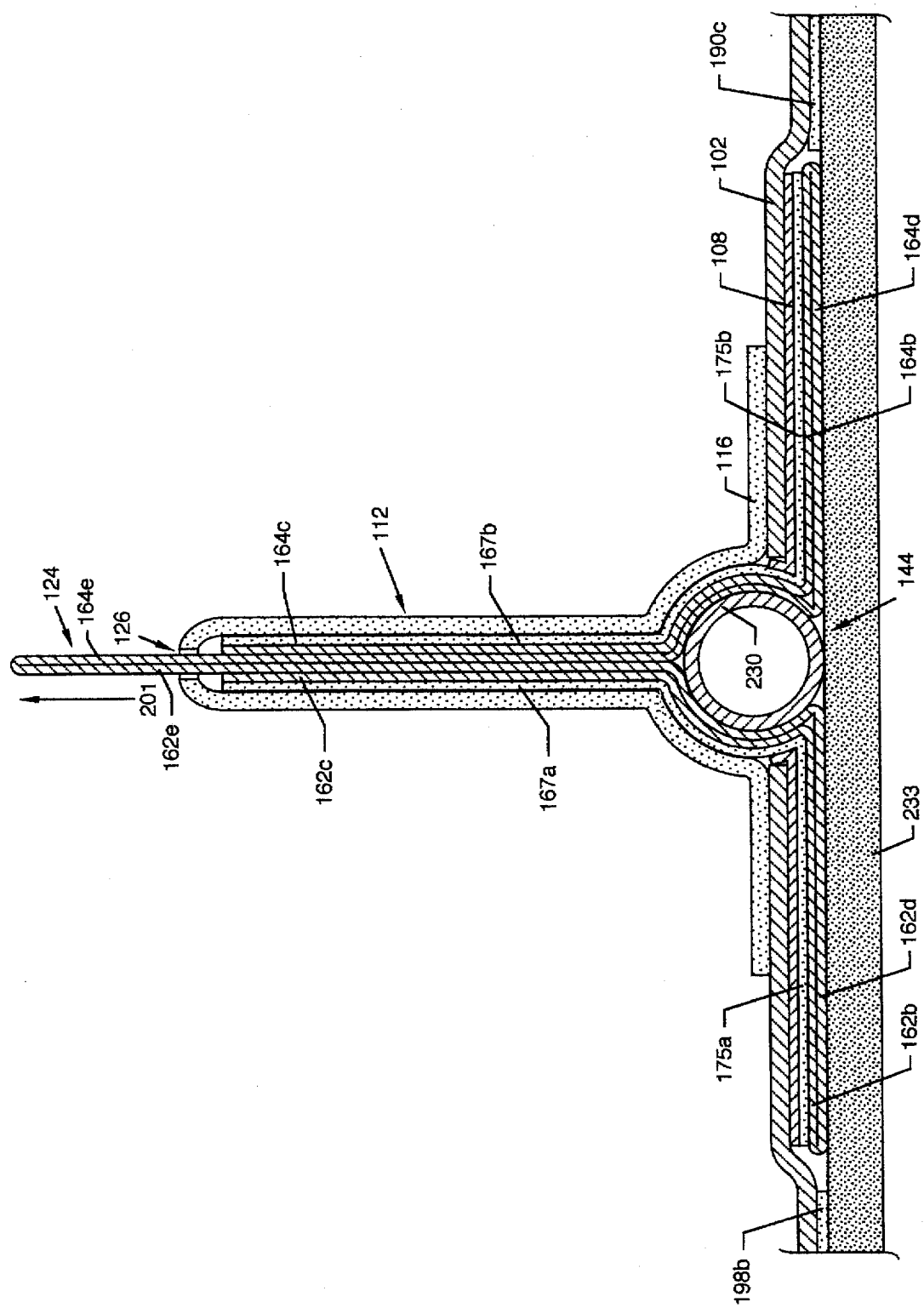

INTRAVENOUS BANDAGE

CROSS REFERENCES TO CO-PENDING APPLICATIONS

None.

BACKGROUND OF THE INVENTION

Field of the Invention

The present invention pertains to a medical device, and more particularly, pertains to an intravenous bandage for the secure capture of an intravenous administration tube and subsequent connection to an IV cannula.

Description of the Prior Art

In general, connection of an administration tube to an IV cannula and a patient's epidermis consisted of taping an administration tube to the epidermis by various quantities of surgical tape subsequent to connection with the cannula. Sometimes, the administration tube would include a taped-down loop or, in the alternative, the tube would be straight and unbent. Inadvertent movement of the patient or of the administration tube could cause the straight tube to reposition, thus disconnecting from the cannula hub, or even worse yet, pulling the cannula and hub from the puncture. The taped loop method offers a buffer zone having more give and a lesser tendency to pull away from the puncture site when the tube was inadvertently repositioned. Poor taping and securement techniques, in any case, did not foster a completely desirable attachment and securement, as often the loops would kink or would catch and would tend to dislodge. Often the puncture site was left uncovered, thus exposing the puncture site to the environment where airborne or other contaminants could come in contact with the puncture site. Previously, tape segments were procured after making the tubing-cannula connection which leaves the cannula uncovered. Pretorn tape also necessitated tape storage in a non-sterile environment. Currently, used tape lacks the adhesive strength of products where the adhesive surface is faced by backing. Often the tape is of the multiple use variety and is non-sterile. Often tubing is attached to the cannula, but is temporarily unsecured. Current membranes waste packing. Current techniques for anchoring an IV administration device do not dependably and completely isolate the puncture site or fully secure the IV administration tubing. Clearly, what is needed is an IV administration securement device which secures and positions for connection to a hub and cannula, and which also provides protection of the puncture site from contamination.

Advantages of Current Invention Over Prior Art

Patient Acceptance

The current invention having no open loop is less cumbersome and disposition to kinking is minimized and the bandage is more compact when finished. The current invention renders IV sites uniform from patient-to-patient and from IV-to-IV in a given patient. These factors render the appearance of IV sites less noticeable and less anxiety provoking. It is also possible that with the first and second alternative embodiments, patients will be able to shower or bathe while the IV site stays dry.

Security

Loop closure reduces the chance for catching and accidentally removing the IV during patient activity, transfers or procedures. The possibility of using stronger adhesives in as much as adhesives contact backing rather than the open surface of adhesive-laden materials, and the provision for circumferential bonding to the IV line render the intravenous fluid administration line more securely attached to the patient.

Economy

Preassembly of the fluid administration line into the bandage at a convenient time, possibly in bulk and by providers of a lesser skill, presents economic savings. The provider starting the IV is able to access multiple parts needed in one assembly. The actual deployment is easier and quicker in as much as there is continuous control of the intravenous cannula, and there is a preformed alignment of components obviating the need for the operator to achieve these alignments. There is less expenditure for packaging materials, and cleanup time is reduced as much as these wasted packaging materials do not have to be gathered and disposed of. Because there is less motion of the intravenous cannula relative to the skin, IV sites are longer lived. Because of the loop closure and these stronger adhesives in the first and second alternate circumferential bonding, there are fewer premature dislodgements.

Infection Control

Each bandage is single use. Patient contact surfaces are exposed only as they are deployed. With second and third embodiments, the open space previously present below the fluid administration line is closed to the environment.

SUMMARY OF THE INVENTION

The general purpose of the present invention is an intravenous bandage.

The intravenous bandage is provided pre-folded and packaged for the end user. An understanding of the IV bandage structure is best understood when observing an unfolded IV bandage in the planar position. A backing member having an adhesive coating is divided about an aligned fold line and frangible perforation lines into a pocket securement portion and a dressing membrane portion. The pocket securement portion includes a pocket for capture of a looped portion of an IV administration tube. The dressing membrane portion includes a transparent membrane which centers over and about a hub and cannula at a puncture site. A peel-away backing member in general covers most base material adhesive areas while leaving exposed the pocket, the dressing membrane, and adhesive areas which are used either for initial securement of the IV administration tube or sterile isolation of the folded membrane portion after the pocket securement portion is opened. Longitudinal inner and outer fold lines define planar areas which are folded and brought into contact with each other into mutual adherement by adhesive sealing strips to present a ready to be used form. During use, frangible perforation members are parted and the dressing membrane portion is folded about the fold line to meet the pocket securement portion. Sealed tabs central to the pocket securement are separated to reveal the pocket so that a looped portion of a fluid administration line may be accommodated. The administration tube is then connected to the cannula and hub. The dressing membrane portion is opened and applied to the skin puncture site. The peel-away backing is then removed from both the pocket securement and dressing membrane portions as successive areas are and pressed into adhesive securement with the epidermis, thus anchoring the fluid administration tube and bandage.

One alternate embodiment of the invention includes an umbilicus member for additional securement of an IV fluid administration tube.

Another alternate embodiment of the invention includes a clip securation device for additional securement of an IV fluid administration tube. Also included is a securement portion for the securation of tubing, line or other such appliances.

One significant aspect and feature of the present invention is an IV bandage for securation of an intravenous tube to a patient.

Another significant aspect and feature of the present invention is an IV bandage having a pocket and pocket securation portion for securement of a looped portion of an administration tube.

A further significant aspect and feature of the present invention is an IV bandage having a dressing membrane and dressing membrane portion.

An additional significant aspect and feature of the present invention is an IV bandage having frangible perforations and a fold line dividing the pocket securation portion and the dressing membrane portion, as well as other tab members.

Still another significant aspect and feature of the present invention is an IV bandage which covers and seals a puncture site.

Still another significant aspect and feature of the present invention is an IV bandage having a transparent dressing membrane and securing base material through which a puncture site inspection can be made.

Another significant aspect and feature of the present invention is an IV bandage having sealing areas about its periphery.

Yet another significant aspect and feature of the present invention is in the form of a first alternative embodiment in which the IV bandage includes a series or housings in which a capture loop positions a fluid administration line into an intermediate surrounding housing which, with other members, forms an umbilicus for support of the fluid administration line adjacent to a puncture site.

Another significant aspect and feature of the first alternative embodiment of the present invention is a one piece removable backing member which reveals adhesive material in a surrounding intermediate housing so that the intermediate housing can adhere as an umbilicus member about the circumference of the fluid administration line.

Yet another significant aspect and feature of the present invention is in the form of a second alternative embodiment where a spring-like clip accommodates a prepackaged or user provided line, fluid administration tube or any other member or styles of appliances in concert with adjacent captive areas.

Yet another significant aspect and feature of the second alternative embodiment of the present invention is a spring-like clip which includes a thin collapsible arcular member and other adjacent arcular members to which an expansion shroud is attached for accommodation of a hub and adjacent members.

Still another significant aspect and feature of the second alternative embodiment of the present invention is an adhesive layer interior to the spring-like clip which secures the fluid administration tube or other like members to the clip.

Still another significant aspect and feature of the second alternative embodiment of the present invention is a removable backing strip which covers the clip adhesive and adjacent adhesive areas until adhesion to a fluid administration tube or the like is desirable.

Having thus described one or more embodiments of the present invention, it is the principal object of the present invention to provide an intravenous bandage.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 16A illustrates a vertical cross section view through the intermediate housing member in the region of the one piece removable backing member just subsequent to the inclusion therein of the fluid administration tube;

DETAILED DESCRIPTION OF THE PREFERRED EMBODIMENTS

Figure 1A:
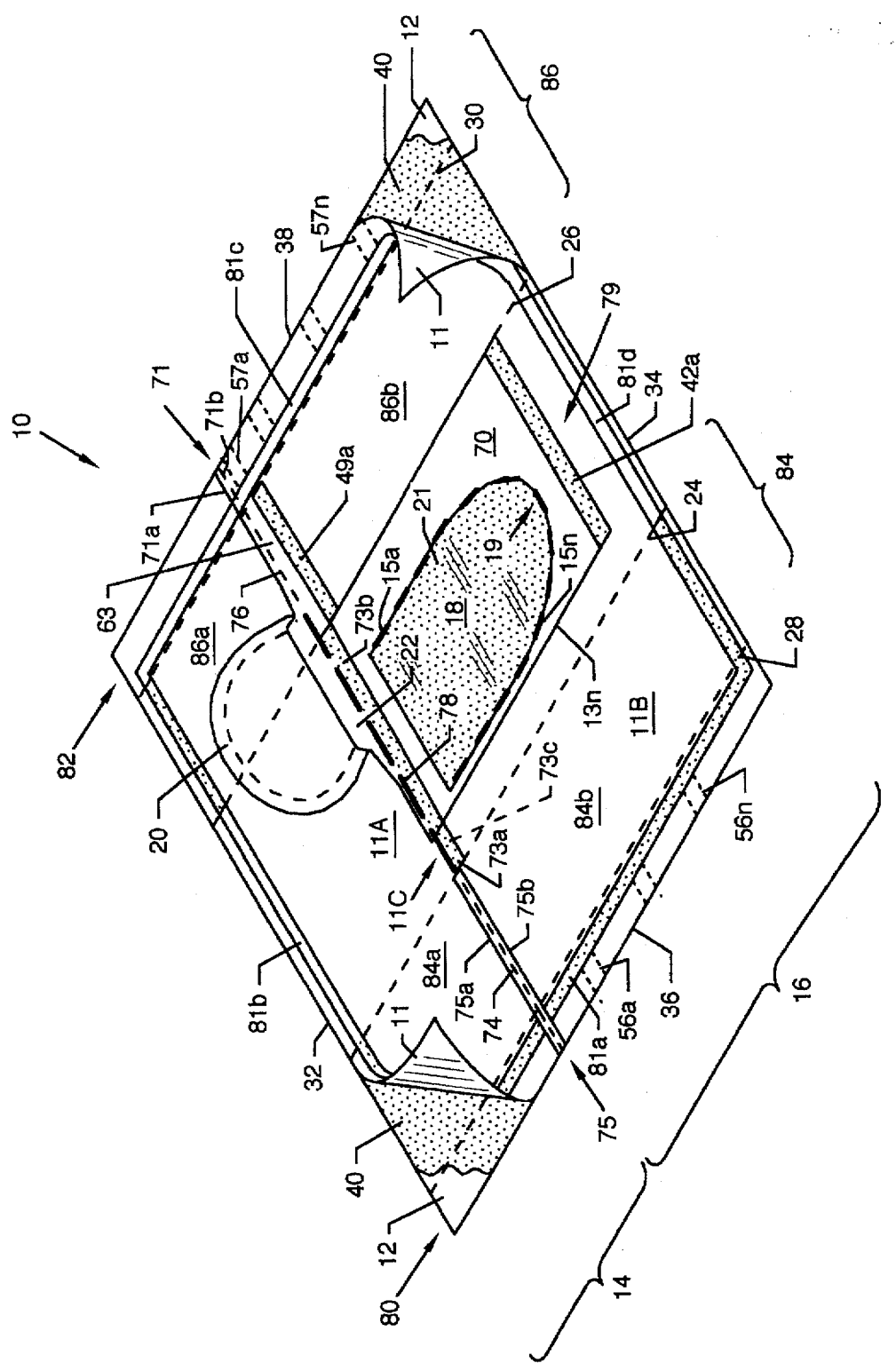
FIG. 1A illustrates an isometric view of an intravenous bandage, the present invention, in an unfolded position.
Figure 1B:
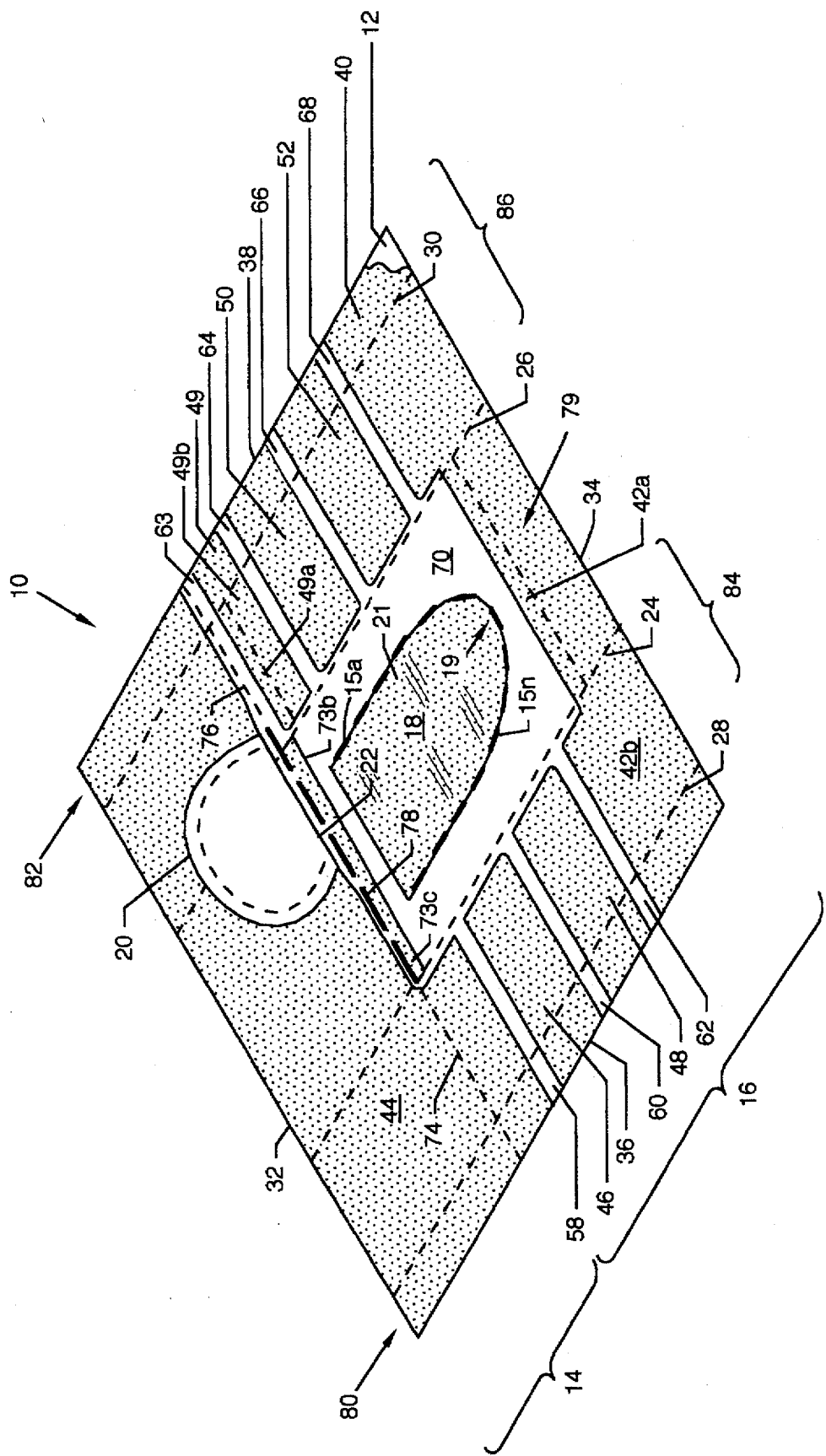
FIG. 1B illustrates an isometric view of the intravenous bandage with the peel-away backing removed.

FIGS. 1A and 1B illustrate perspective views of an intravenous bandage 10, the present invention, in an unfolded position. FIG. 1A illustrates the IV bandage 10 with peel-away backing 11 adhering to the inner surface of the IV bandage 10. FIG. 1B illustrates the IV bandage 10 with the peel-away backing 11 removed. The IV bandage 10 is fabricated about a pliable, flexible and transparent base material 12, a polymer material for a planar base or other materials known in the art which are medically compatible with skin of a person. Preferably, the material is substantially transparent. The base material overlying the region of the dressing membrane 18 is transparent. The IV bandage 10 in general is divided into continuous and adjacent pocket securement and dressing membrane portions 14 and 16 respectively. Central to the IV bandage 10 and also to the dressing membrane portion 16 is a transparent dressing membrane 18 through which inspection of the skin puncture site can be made subsequent to application of the IV bandage 10. Transparent dressing membrane 18 in general resembles a rectangular member, one end of which draws to a point 19. The dressing membrane 18 is intermittently sealed at sealing areas 15a–15n to the flexible base material 12 in a manner to incorporate a plurality of openings between the base material 12 and the membrane 18. The openings vent the area between the membrane 18 and the overlying base material 12. An arced pocket 20 having an opening 22, fashioned of a suitable material aligns along and about the pocket securement portion 14 of the IV bandage 10 for capturing of a fluid administration line 92, illustrated in FIG. 4. The arcular edge of pocket 20 describes a curve in excess of 180 degrees for purposes of capture of a fluid administration line 92. Longitudinal fold lines are positioned parallel to the longitudinal axis of the IV bandage 10 and include factory made inner fold lines 24 and 26 and factory made outer fold lines 28 and 30, each of which intersect left and right edges 32 and 34 of the base material 12. Edges 36 and 38 align between the ends of the left and right edges 32 and 34. A peel-away backing 11, continuous over large areas of dressing membrane portion 16 and pocket securement portion 14 is provided to protect defined areas of adhesive 40 on the inner surface of the base material 12. The backing 11 is subdivided into backing portions 11A and 11B. An essentially U-shaped backing member portion 11B aligns over the majority of the dressing membrane portion 16 and along edge 34 and between portions of edges 36 and 38 leaving the area over and around dressing membrane 18 uncovered. Dressing membrane adhesive 21 is located on the inner (skin contact) surface of dressing membrane 18. Dressing membrane adhesive 21 comes in contact with opposing planar peel-away backing areas 84b and 86b, as they are folded about inner fold lines 24 and 26 during manufacture. A rectangular adhesive area 42a with adhesive 40 on the base material 12 is exposed as illustrated in FIG. 1A. Peel-away backing 11B connects to peel-away backing portion 11A via a narrow neck of backing material 11C bridging fold line 78. Peel-away backing portion 11A covers major portions of the pocket securement portion 14 except pocket 20. Adhesive area 44 aligns along edge 32 and along a portion of edges 36 and 38 but does not include the pocket 20. The end of the adhesive area 44 aligning on edge 36 extends partially onto the dressing membrane portion 16. Rectangular adhesive areas 46 and 48 align along edge 36 and between the inner ends of adhesive areas 42b and 44. Rectangular adhesive areas 49b (which is part of adhesive area 49), 50 and 52 align along edge 38 and between the inner ends of adhesive areas 42b and 44. Adhesive-free areas 58, 60 and 62 are located between areas 44, 46, 48 and 42b, and adhesive-free areas 63, 64, 66 and 68 are located between adhesive areas 44, 49a–49b, 50, 52 and 42b. Adhesive-free areas 58, 60, 62, 63, 64, 66 and 68 intersect an adhesive-free rectangular area 70 surrounding dressing membrane 18. The areas 58, 60, 62, 64, 66, 68 and 70 are free of adhesive to allow ventilation from ambient air to the space between the dressing membrane 18 and the base material 12 when applied to the skin. Adhesive-free space 63 secures to a portion of adhesive area 73b when the bandage is folded. Adhesive 56a–56n on the side of the peel-away backing member lib directly in contact with base material 12 extends inwardly from the edge 36 in sealing alignment with the outer portions of the adhesive-free areas 58, 60 and 62, respectively to provide for sterile sealing of the adhesive free areas 58, 60 and 62. In a similar fashion, adhesive 57a–57n also on peel-away backing member 11B extends inwardly from the edge 38 in sealing alignment with the outer portion of the adhesive-free areas 63, 64, 66 and 68 respectively to provide for sterile sealing of the adhesive-free areas 63, 64, 66 and 68. Exposed adhesive area portions 42a, 73a and 73b align perpendicular to opposing ends of the dressing membrane 18. Another adhesive area 73c on the base material 12 aligns beneath the narrow neck of backing material 11C having adhesive material 73a and is exposed with the removal of the backing material 11C when the backing material 11A, 11B and 11C is removed. The adhesive area 73c aligns to the right of the fold line 78 on base material 12 and extends between fold line 24 and adhesive area 73b. Frangible perforation 74 through the base material 12 aligns perpendicularly between edge 36 and inner fold line 24 and adjacent to a slit 75 in the peel-away backing 11 having edges 75a and 75b, and, in a like and similar fashion, frangible perforation 76 aligns through the base material 12 perpendicularly between edge 38 and inner fold line 26 and adjacent to a slit 71 in the peel-away backing 11 having edges 71a and 71b. An exposed adhesive area 49a, part of adhesive area 49, is revealed between adhesive-free area 63 and the edge of peel-away backing portion lib as illustrated in FIG. 1A. A fold line 78 illustrated as a long heavy dashed line, aligns along the axii of and between the inner ends of frangible perforations 74 and 76. IV bandage 10 is folded during the manufacturing process about fold lines 24, 26, 28 and 30 to form a ready-to-use IV bandage 10 in sterile form such as illustrated in FIG. 2.

Planar areas are defined between various edges and fold lines during the manufacturing process. The planar area 79 lies between the inner fold lines 24 and 26. To achieve the form illustrated in FIG. 2, beginning with the bandage 10 in planar form as in FIG. 1A, folds are firstly made downwardly about outer fold line 28 to form a rectangular planar tab 80 extending outwardly from the outer fold line 28 to edge 36, and another fold is made about outer fold line 30 to form a rectangular planar area tab 82 extending outwardly from the outer fold line 30 to edge 38. Rectangular area planar portions 84 and 86 are the areas between folds 24–28 and 26–30, respectively. Secondly, folds are made upwardly about inner fold lines 24 and 26 to bring rectangular planar area portions 84 and 86 into close intimate contact with the planar area 79. As this action occurs, the planar area tabs 80 and 82 are juxtaposed in intimate vertical contact and held together by mutual contact of opposing areas of sealing strip members 81a–81d.

Adhesive areas of separable and partible adhesive align along, about or in close proximity to the outside edges of the peel-away backing 11 and at the juncture of the backing to itself where fold lines 28 and 30 meet to secure planar members as described herein. A continuous sealing strip consisting of sealing strip areas 81a–81d aligns as follows: sealing strip area 81a aligns on the peel-away backing 11 in close proximity to fold line 28, sealing strip area 81b aligns on the peel-away backing 11 in close proximity to edge 32, sealing strip 81c aligns on the peel-away backing 11 in close proximity to fold line 30, and sealing strip 81d aligns on the peel-away backing 11 in close proximity to the edge 34. The sealing strip 81 lies on the side of the peel-away backing 11 which in the unfolded position is away from the base material 12. Sealing strip area 81b is folded about fold lines 24 and 26 into mutual self-contact along and about the edge 32, and sealing strip area 81d in like manner, is folded about fold lines 24 and 26 into mutual self-contact along and about the edge 34. At this time sealing strip areas 81a and 81c are brought into contact for mutual contact of planar tab areas 80 and 82. Sealing strip area 81a is adhesive covered. Sealing strip areas 81b and 81d are adhesive covered from their junction with area 81a to fold line 24 and between inner fold line 26 and outer fold line 30. Sealing strip area 81c is adhesive free. The use of adhesives and folding as described provides for a sealed interior thus maintaining sterility of the pocket securement and dressing membrane portions 14 and 16 respectively. Additional sealing of the dressing membrane portion 16 exists to provide and maintain a sterile dressing membrane area environment when the dressing membrane and pocket securement portions 16 and 14 are fractured along and about frangible perforations 74 and 76. As seen in FIG. 1A, the strip of exposed adhesive 73b continues in the same width a short distance towards fold line 24 as 73a on the narrow neck of backing material 11C of peel-away backing 11 which at that region serves to join peel-away backing members 11A and 11B. This is the only area of adhesive attached to the inner surface of the backing 12 central to the marginal sealing strip. In the factory folded position, the peel-away backing's margin 75b between folds 24 and 28 is in adhesive contact with adhesive area 73a and an adjacent portion of adhesive area 73b. In the factory-folded position, the base material adhesive-free area 63 between fold 30 and fold 26 is in adhesive contact with the adjacent portion of adhesive area 73b.

Figure 2:
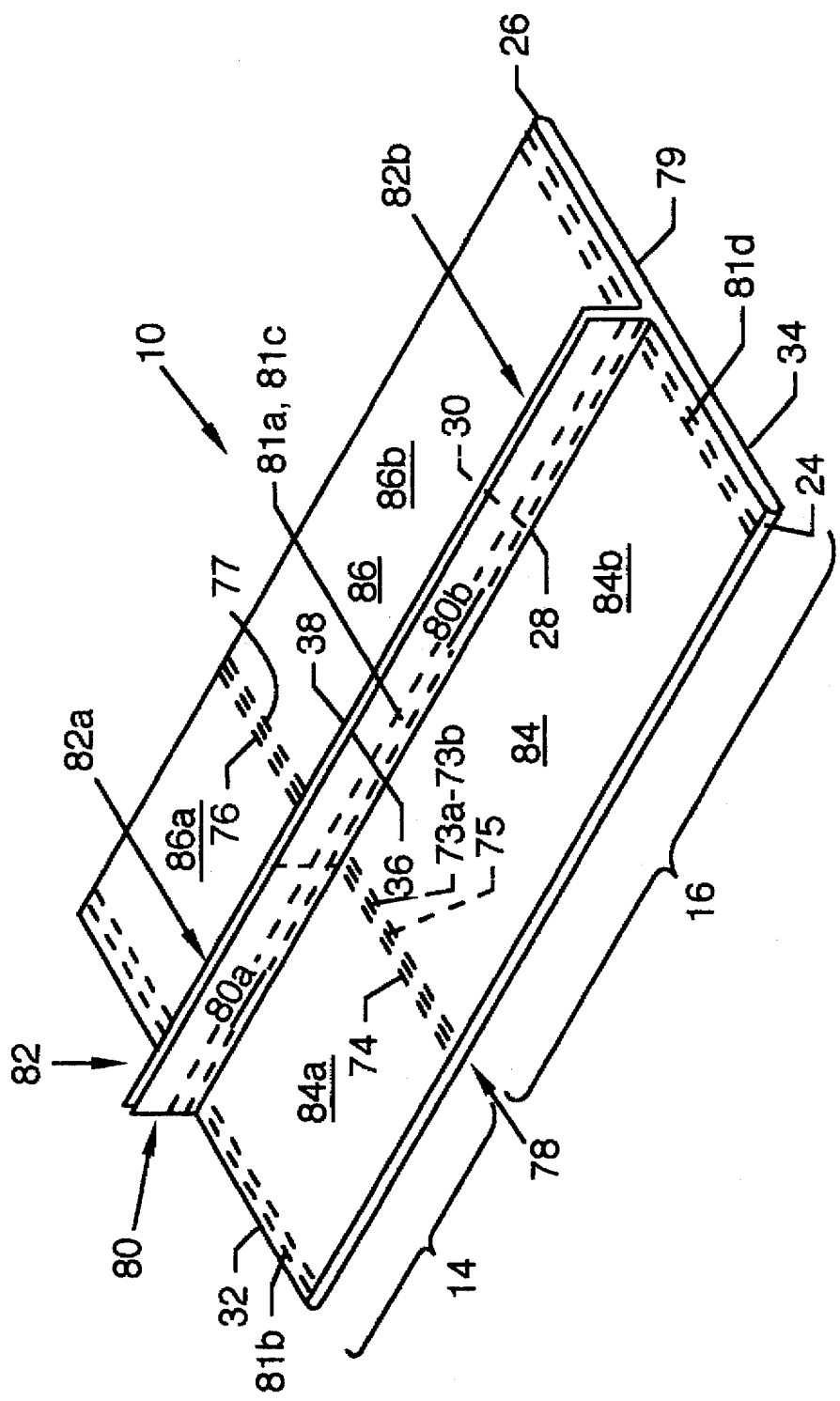
FIG. 2 illustrates a ready-to-use bandage in sterile form prior to use.

FIG. 2 illustrates a perspective view of the IV bandage 10, all numerals corresponding to elements previously described. The IV bandage 10 is illustrated ready for the application process. Tabs 80 and 82 have been folded upwards from their delivery and storage position. The planar area tab 80 is divided about the vertical portion of the frangible perforation 74 to form planar tab portions 80a and 80b, and planar tab area 82 is divided about the vertical portion of frangible perforation 76 to form planar tab areas 82a and 82b. Planar area 84 is divided about the horizontal portion of the frangible perforation line 74 to form planar areas 84a and 84b. Planar 86 is divided in a like manner about the horizontal portion of the frangible perforation line 76 for form planar areas 86a and 86b. Planar tab portions 80a–82a are manually and simultaneously grasped just to the left of the vertical portions of the frangible perforations 74–76, each of which includes horizontal and vertical components. In a similar, mirror-like fashion, planar tabs 80b–82b are simultaneously grasped just to the right of the vertical portions of the frangible perforations 74–76. Tension is exerted to cause the vertical portions of perforations 74 and 76 extending through the base material 12 to part.

Figure 3:
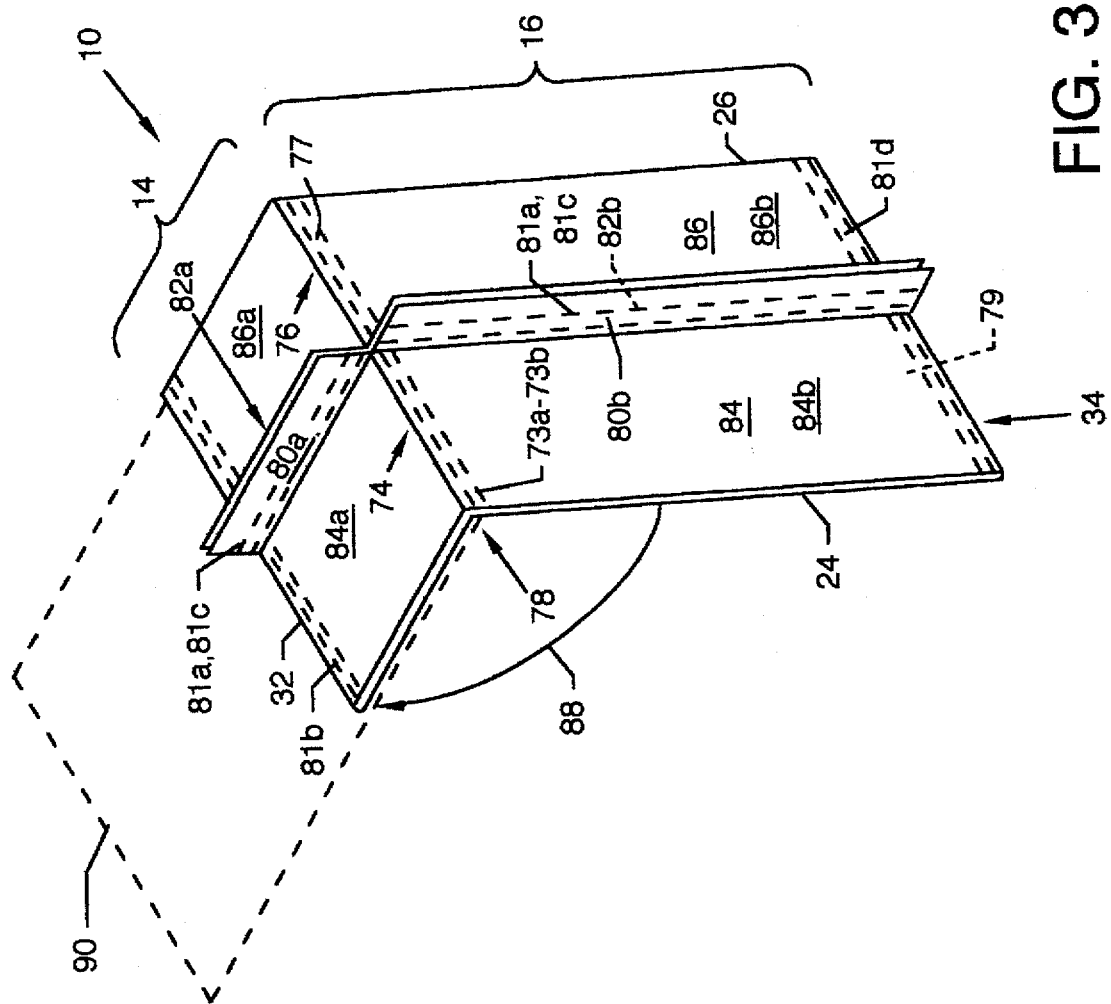
FIG. 3 illustrates initial separation and bending of the dressing membrane about a fold line.

FIG. 3 illustrates initial separation and bending of the dressing membrane portion 16 from the pocket securement portion 14 about the fold line 78, all numerals corresponding to elements previously described. The dressing membrane portion 16 can now be rotated about the fold line 78 as indicated by arrow 88 to a position illustrated by dashed line 90.

Figure 4:
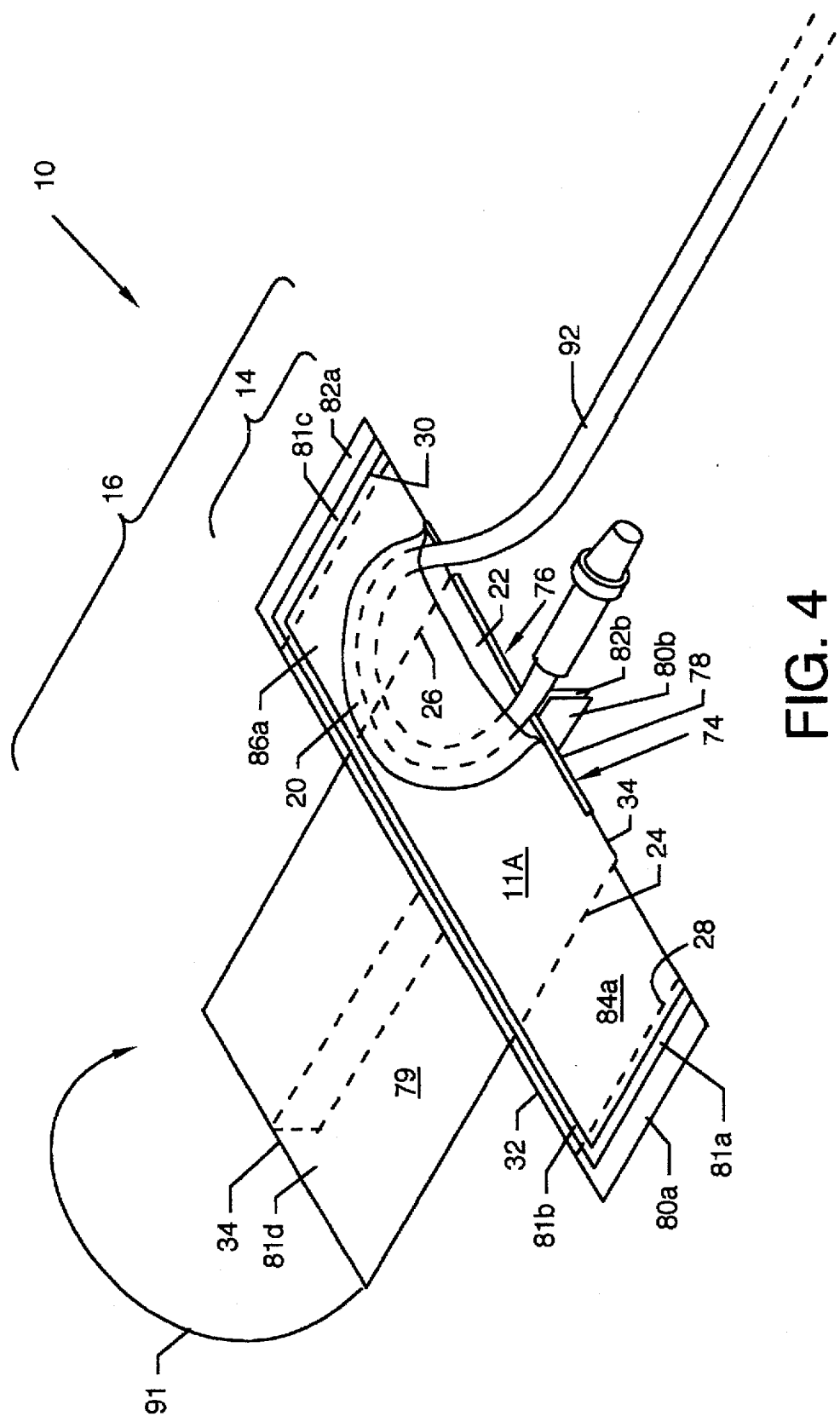
FIG. 4 illustrates a fluid administration line aligned in the pocket of the pocket securement portion.

FIG. 4 illustrates fluid administration line 92 aligned in the pocket 20 of the pocket securement portion 14, all numerals corresponding to elements previously described. Planar tab portions 80a and 82a, frangible perforations 74 and 76, and sealing strip area 81b have been separated as planar areas 84a and 86a are folded back to expose pocket 20 and its opening 22. A loop has been formed near the distal end of the fluid administration line 92 and inserted into the opening 22 of the pocket 20. An appropriate length of fluid administration line 92 extends out of the pocket 20 to connect to an IV cannula hub. After grasping tabs 80b and 82b rotation per arrow 91, of bandage 10 about the folded membrane portions long axis is the next step and results in FIG. 5.

Preparation to this point could be performed by some of the lesser skilled personnel in a health care institution just prior to or well in advance of final deployment. As an alternative, manufacturers of fluid administration lines could deliver their product assembled with the current invention at this stage of deployment.

Figure 5:
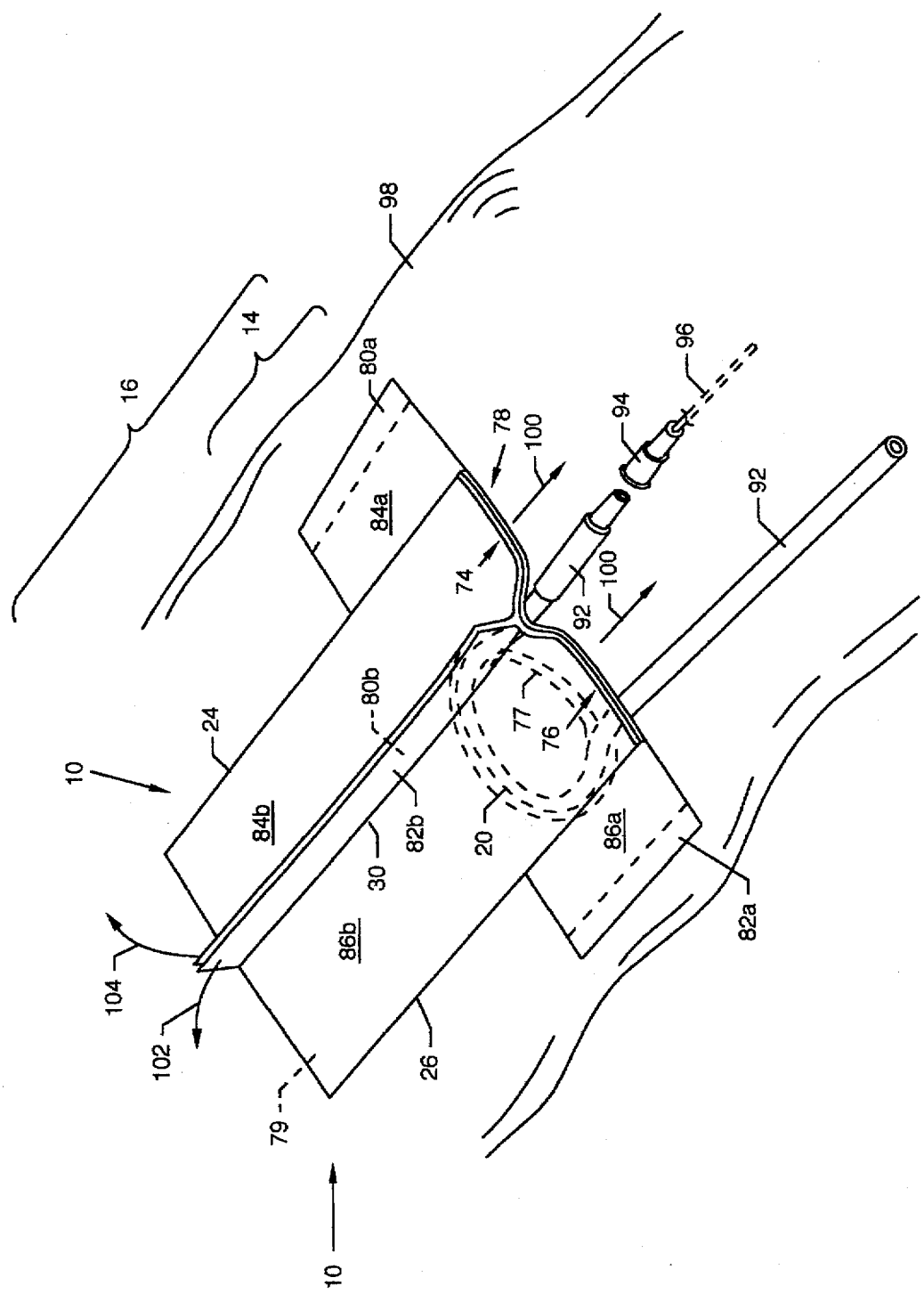
FIG. 5 illustrates the IV bandage and fluid administration line immediately prior to connection to a hub.
Figure 6:
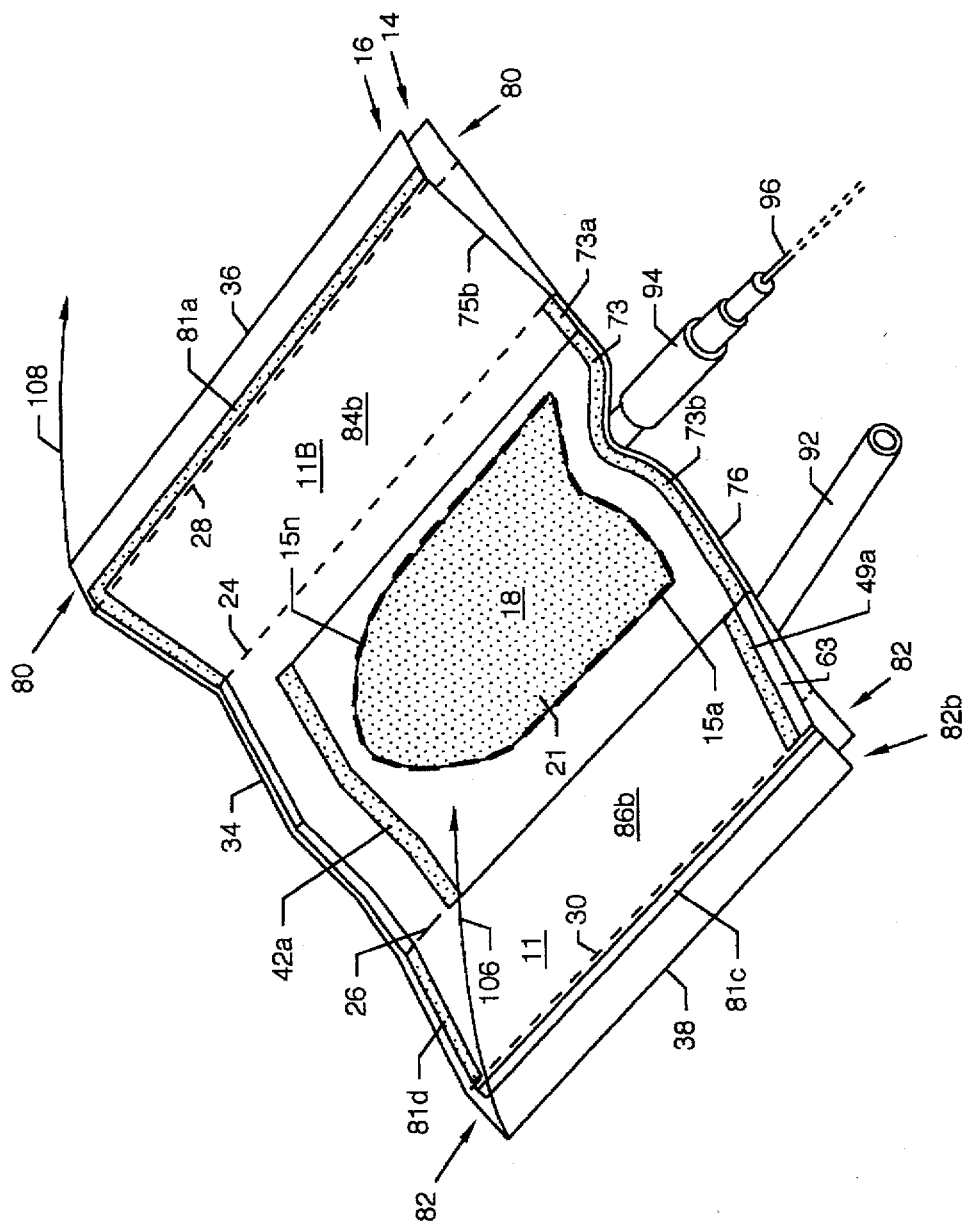
FIG. 6 illustrates the fluid administration line connected to the hub just prior to rotation of the dressing membrane portion over the puncture site.

FIG. 5 illustrates an IV bandage 10 and fluid administration line 92 immediately prior to connection to the hub 94 of an intravenous cannula 96 in a patient's arm 98, all numerals corresponding to elements previously described. The IV bandage 10 with the attached fluid administration line 92 is grasped by the planar tab portions 80b and 82b in the area just above the pocket 20 to act as a handle. Connection of fluid administration line 92 to intravenous cannula hub 94 is performed as indicated by arrow 100. Subsequent to fluid administration line/cannula hub connection, planar tab areas 80b and 82b are drawn apart, the motions being perpendicular to the long axis of the bandage, away from the midline, and in a plane parallel to the dressing membrane portion 16. The seal formed by membrane portion 16, parts of sealing strip areas 81a and 81c is thus opened. Continuing the same motion draws planar areas 84b and 86b from contact with planar area 79. Adhesive areas 73a–73b, sealing strip area 81d, the sterile dressing membrane 18 and adhesive areas 42a and 49a are thus exposed for the first time. The bandage appears now as in FIG. 6. With peel-away backing 11 in place, the dressing membrane portion 16 is rotated about fold line 78 as per arrows 106 and 108. The dressing membrane 18 captures, covers and seals the fluid administration line/cannula hub 92 juncture and skin puncture sites. Adhesive 42a, 49a and 73b secure fluid administration line 92 as it enters the membrane portion of the bandage and as it enters the pocket 20 and as it leaves the pocket 20 respectively. With the fluid administration line 92 positionally secured, the peel-away backing 11 is grasped with one hand at the end of planar tab 82b nearest fold line 78 and evolves with a counter-clockwise motion as the opposite hand applies counter-traction on the outside of the bandage and presses successively exposed adhesive areas into firm skin contact. If the IV site is near a joint such that the pocket securement portion 14 would lie beyond the joint, adhesive surfaces of 84a and 86b would in succession be folded under and applied to what would otherwise be the skin contact surface of the pocket securement portion.

Figure 7:
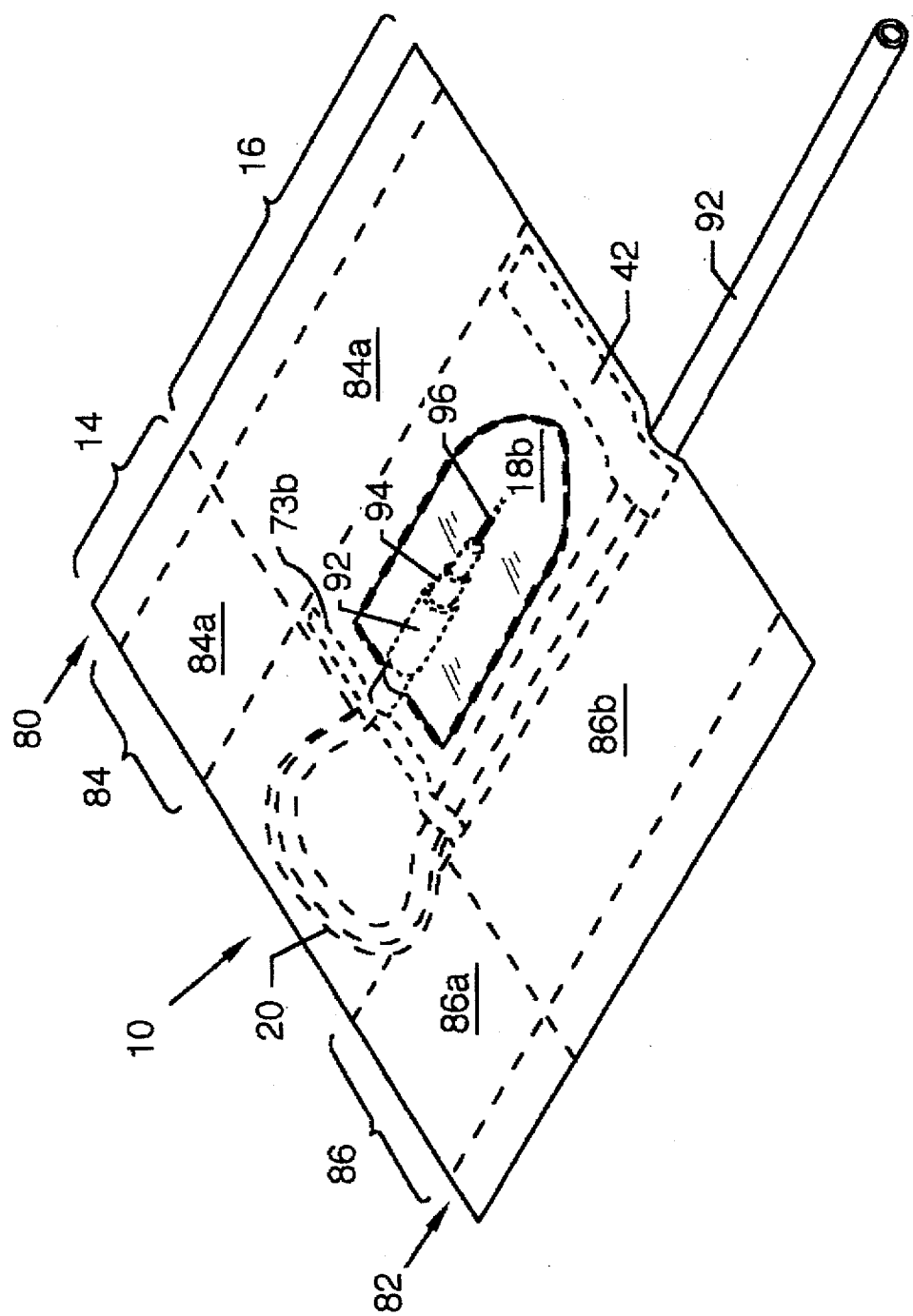
FIG. 7 illustrates the IV bandage securing the fluid administration line to a cannula hub at a skin puncture site.

FIG. 7 illustrates the IV bandage 10 securing a fluid administration line 92 to a cannula hub 94 at a skin puncture site, all numerals corresponding to elements previously described.

DETAILED DESCRIPTION OF THE FIRST ALTERNATIVE EMBODIMENT

Figure 8:
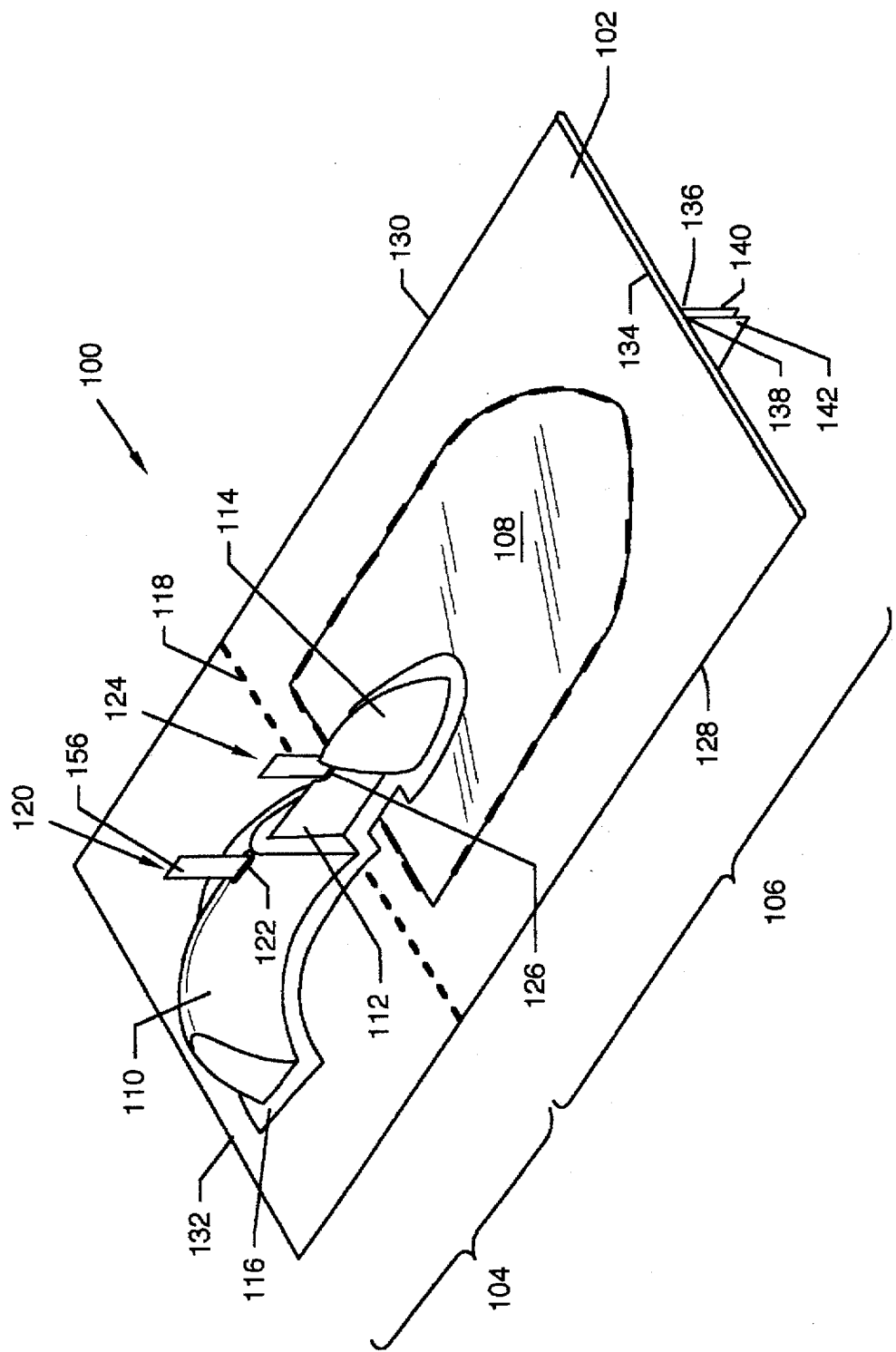
FIG. 8, a first alternative embodiment, the subject or which is also included in FIGS. 9 through 18, illustrates an isometric unfolded view of an intravenous bandage for anchoring of an administration line by an umbilicus to the skin and for protecting the skin puncture site.
Figure 12:
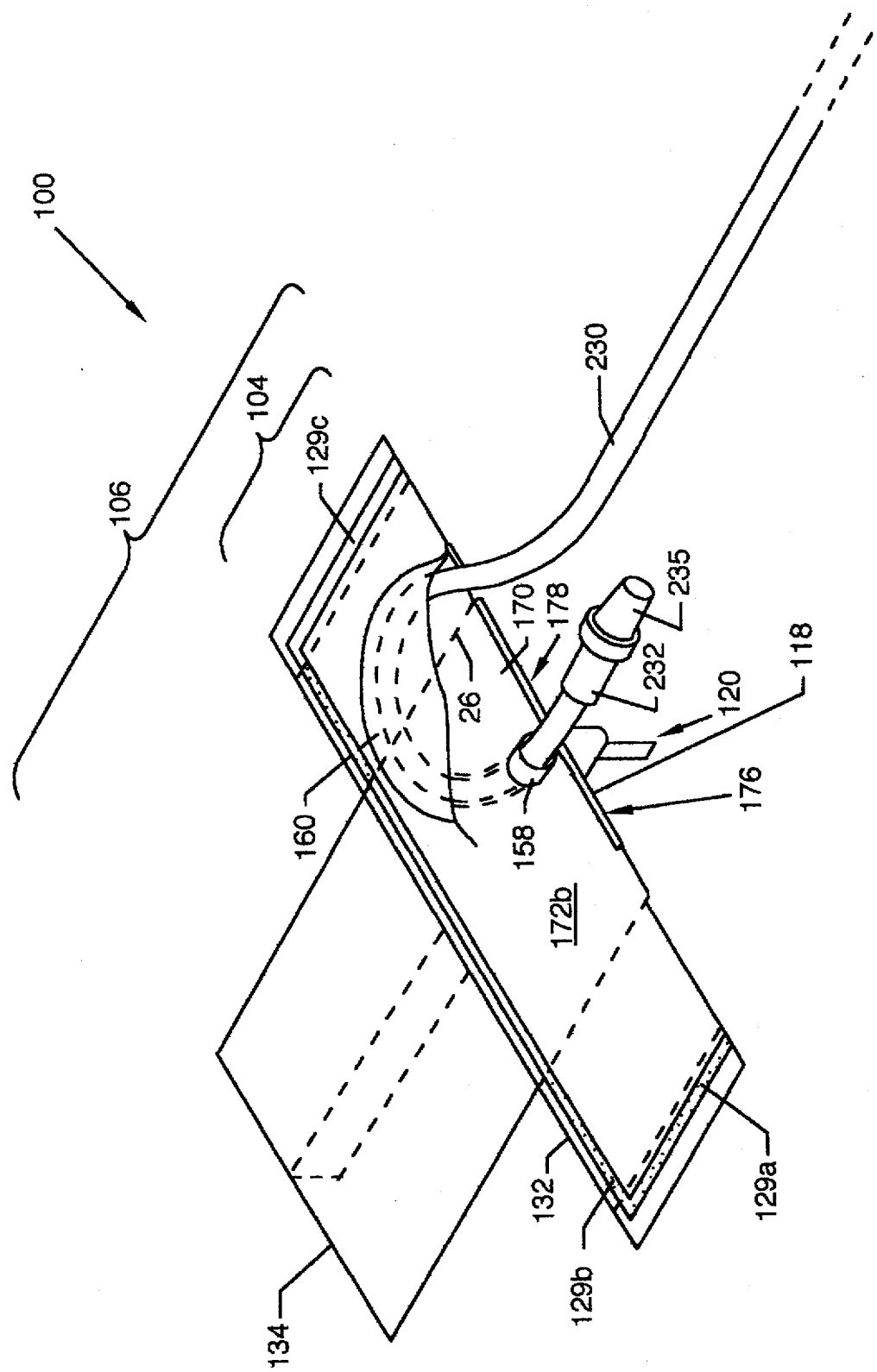
FIG. 12 illustrates a fluid administration line positioned in a pocket and through a capture loop.

FIG. 8, a first alternative embodiment, illustrates a perspective view of an intravenous bandage 100 as presented for anchoring a fluid administration line 230, illustrated in FIG. 12, to the skin and for protecting the skin puncture site. As with bandage 10, bandage 100 conveniently attaches as a handle to tubes or lines in advance of their connection to patients, is single use and accomplishes both sterile dressing and anchoring functions in a fashion economical of time, motion and materials. IV bandage 100 incorporates the design features of IV bandage 10 and adds to them elements to further reduce; (1) the risk of tension on the fluid administration line dislodging the indwelling cannula; and (2) the chances of contamination of the skin puncture site. IV bandage 100 adds to IV bandage 10 pliable and bendable raised housing members 110, 112 and 114 into which a fluid administration line 230 is positioned. The pliable and bendable housing members 110, 112 and 114 facilitate circumferential bonding of bandage 100 to the distal end of a fluid administration line 230 and attachment of a fluid administration line 230 to the skin via an umbilicus 234, illustrated in FIG. 14. The IV bandage 100 provides isolation of the skin puncture site over and above that provided by IV bandage 10. This increment in protection from the environment results from closure of the space between the fluid administration line 230 and the skin in close proximity to the skin puncture site. In keeping with the scope of the invention, other types of lines could be so secured. During the deployment process, protective backing is removed from the interior of the adhesive-laden intermediate housing member 112 and from adjacent planar areas to provide for adhesive anchoring of a fluid administration line 230 to an umbilicus 234 and of the umbilicus to the skin adjacent to IV cannula.

Illustrated in FIG. 8 is the intravenous bandage 100 having a base material 102 which is divided generally into a pocket portion 104 and a dressing membrane portion 106. A transparent dressing membrane 108 is located central to the dressing membrane portion 106. Major and minor pliable, flexible, and bendable housing members 110 and 114, having an intermediate flexible and bendable housing member 112 align to the planar portions of the intravenous bandage 100. The major housing member 110, the minor housing member 114, and the intermediate housing member 112 are surrounded by a continuous flange member 116 about the base of the members which secures such as by gluing or welding to the base material 102 pocket and dressing membrane portions 104 and 106. Major housing member 110 aligns and secures to the pocket portion 104 and generally to the left of a fold line 118 shown in heavy dashed lines, and the intermediate housing member 112 aligns generally to the right of the fold line 118 and secures to the dressing membrane portion 106. The minor housing member 114 aligns and secures to the dressing membrane portion 106. Dressing membrane 108 along its margin paralleling fold line 118 is bonded to base material 102. Where both dressing membrane 108 and base material 102 lie adjacent to continuous flange 116, they are similarly bonded. Major and minor housing members 110 and 114 and the intermediate housing member 112 accommodate a fluid administration line or other indwelling line. Major housing member 110 is in the form of a horizontally aligned arc to accommodate a fluid administration line which is initially resident to the underlying pocket of pocket securement portion 104. Tab portion 156 of positional capture loop 120 extends upwardly through slit 122 and downwardly into a pocket 160 in pocket securement portion 104. A one piece removable backing member 124, also illustrated in FIG. 9, extends upwardly through slit 126 at the top edge of the intermediate housing member 112 and downwardly through the membrane portion 106.

Figure 9:
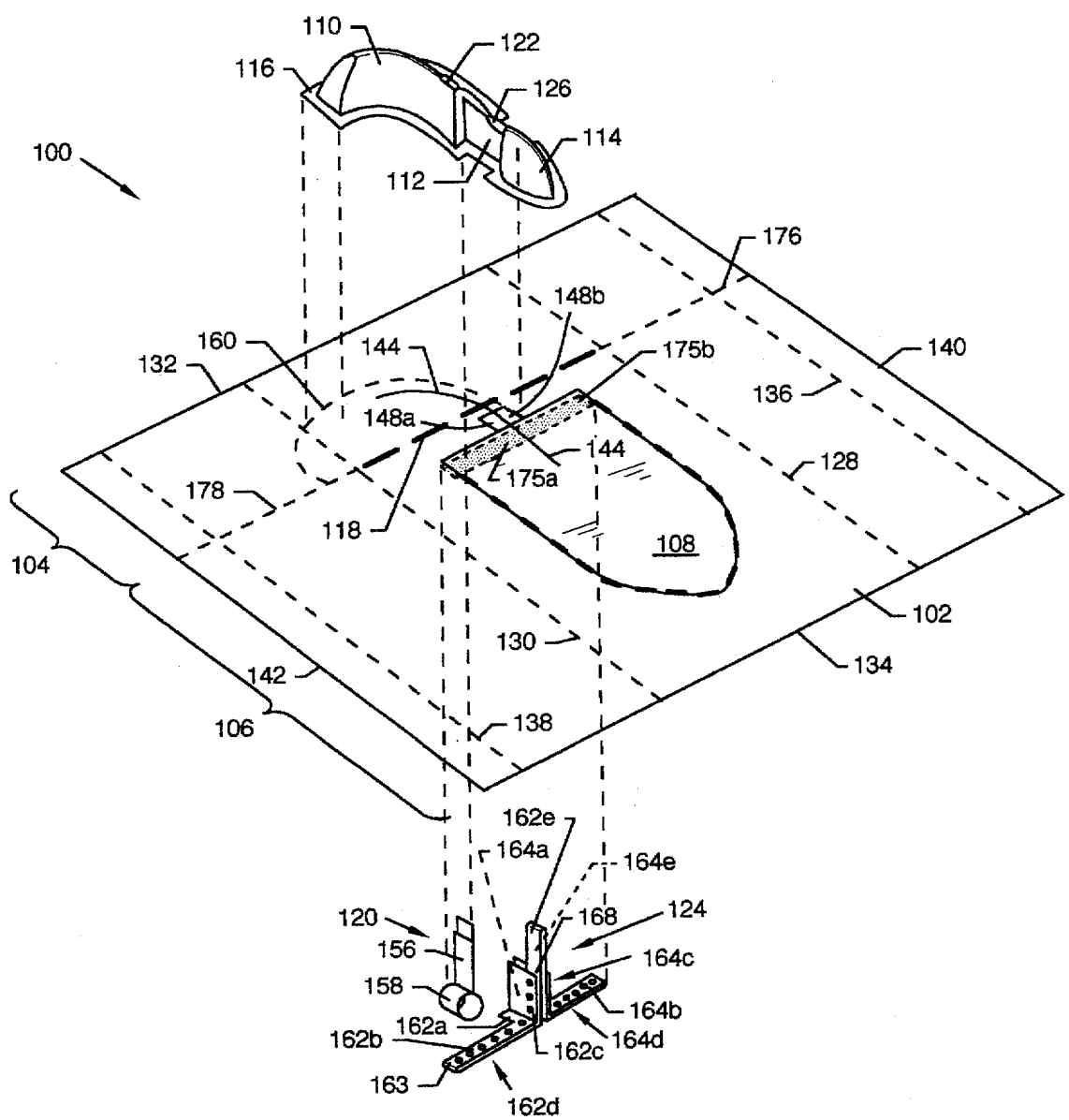
FIG. 9 illustrates an exploded view of the members of the IV bandage of FIG. 8.

FIG. 9 illustrates an exploded view of members of the IV bandage 100, all numerals corresponding to elements previously described. The IV bandage 100 is illustrated in the unfolded position to show multiple fold lines, including inner fold lines 128 and 130 and outer fold lines 136 and 138, all aligned perpendicularly between the left edge 132 and the right edge 134. Fold line 118 aligns perpendicularly between fold lines 128 and 130. Frangible perforations 176 and 178 align along the axis of the fold line 118 and extend to the outer edges 140 and 142 from fold lines 128 and 130 respectively. An arcular slit 144 through the base material 102 corresponding to the orientation of the overlying major housing member 110, intermediate housing member 112, and the overlying minor housing member 114, extends from the pocket securement portion 104 to the dressing membrane portion 106. The dressing membrane portion 106 end of arcular slit 144 also passes through the end of the dressing membrane 108 closest to fold line 118.

The positional capture loop 120 aligns through the base material 102. Capture loop 120 includes a tab portion 156 and a loop portion 158. The loop portion 158 of the capture loop 120 is located beneath the arcular slit 144 on the underside of the base material 102 for capturing a fluid administration line 230. The tab portion 156 extends upwardly through slit 144, the interior of major housing member 110, and finally slit 122.

Figure 16B:
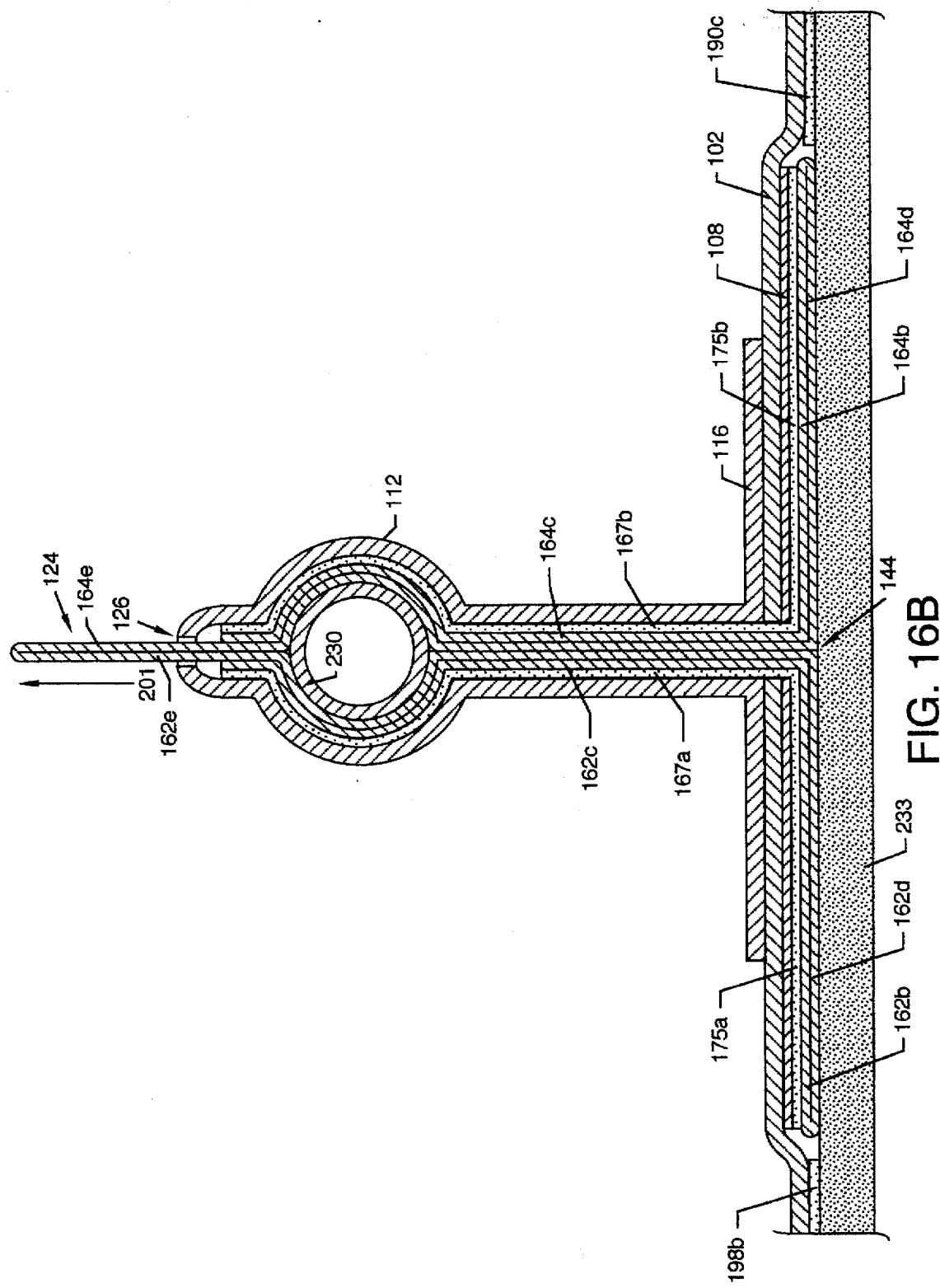
FIG. 16B illustrates the fluid administration positioned in the upper region of the intermediate housing member.
Figure 17:
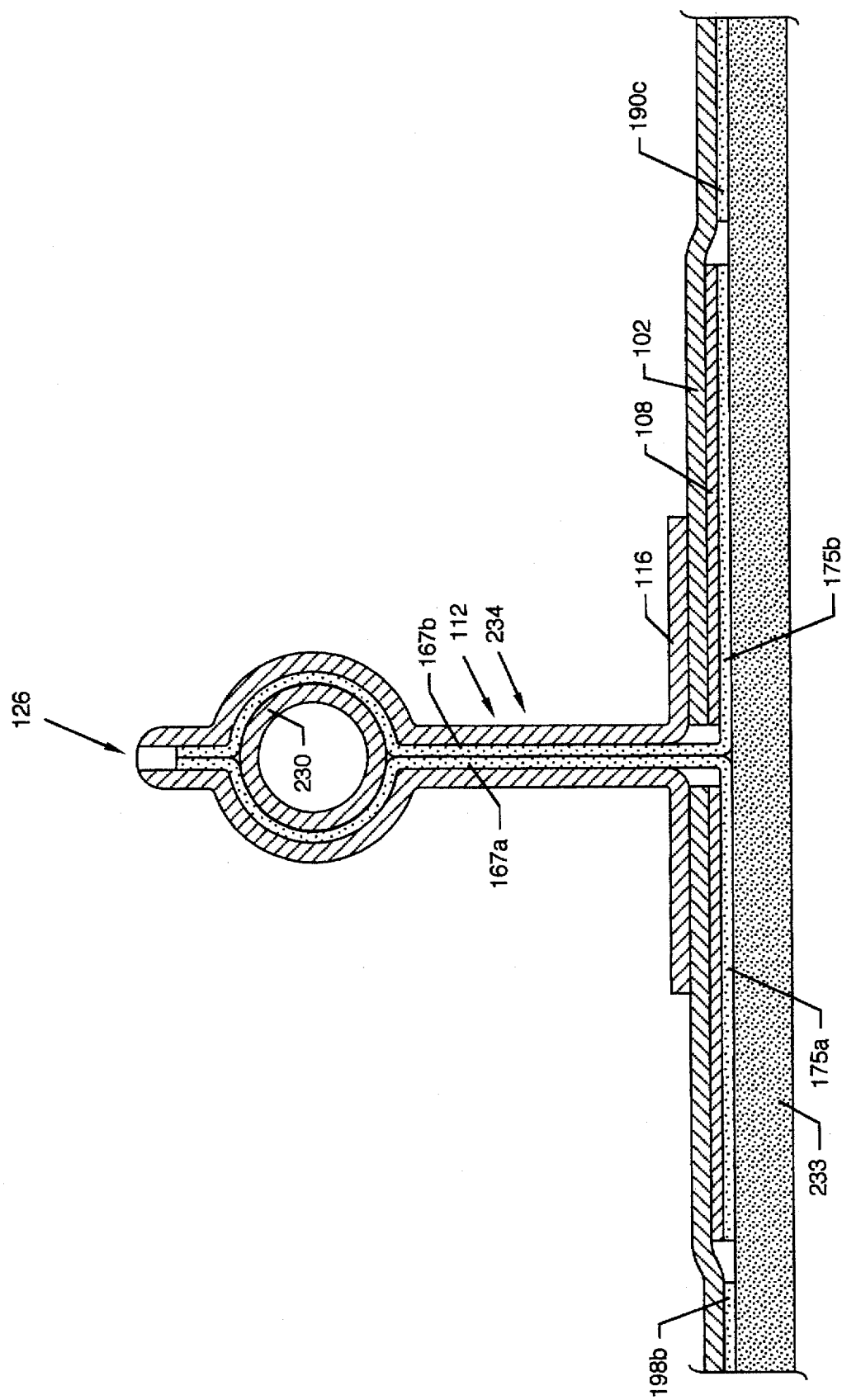
FIG. 17 illustrates the fluid administration tube secured to the epidermis by the umbilicus.

The one piece removable backing member 124 aligns through the arcular slit 144, the transparent membrane 108, and the base material 102, and finally through the slit 126 in the intermediate housing member 112. The one piece removable backing member 124 includes horizontal planar portions 162a–162b and 164a–164b which at their central margins are continuous with vertical planar portions 162c and 164c. Removable backing portions 162b and 164b cover adhesive areas 175a–175b on the underside of transparent membrane 108. Removable backing portions 162a and 164a cover adhesive areas 148a–148b on the underside of base material 102. The horizontal adhesive areas 175a–175b and 148a–148b are contiguous with vertical adhesive areas 167a and 167b of FIG. 16A. The latter are applied to the left and right interior walls of the intermediate housing member 112 as illustrated in FIGS. 16A and 17. The adhesive areas 167a and 167b together with the intermediate housing member 112 and adhesive areas 175a–175b and 148a–148b together with transparent membrane 108 and base material 102 form an umbilicus and provide for attachment to the skin, as illustrated in FIG. 17. A double-layered actuating tab portion 168 of the one piece removable backing member 124 extends through the slit 144 and the membrane 108 and the base material 102 and continues upwardly through intermediate housing member 112 and slit 126. The double-layered actuating tab portion 168 is formed from extensions of the lateral ends of portions of 162b and 164b which fold 180 degrees under themselves to continue centrally as 162d and 164d until meeting beneath slit 144 and fold 90 degrees to extend together vertically as 162e and 164e upward through the interior of intermediate housing member 112 and finally slit 126. Portions 162b–162c and 164b–164c of one piece removable packing member 124 nave a series of holes 163 allowing adhesive areas 175a–175b and 167a–167b to secure removable backing portions 162b–162c and 164b–164c as well as 162d–162e and 164d–164e.

Figure 10:
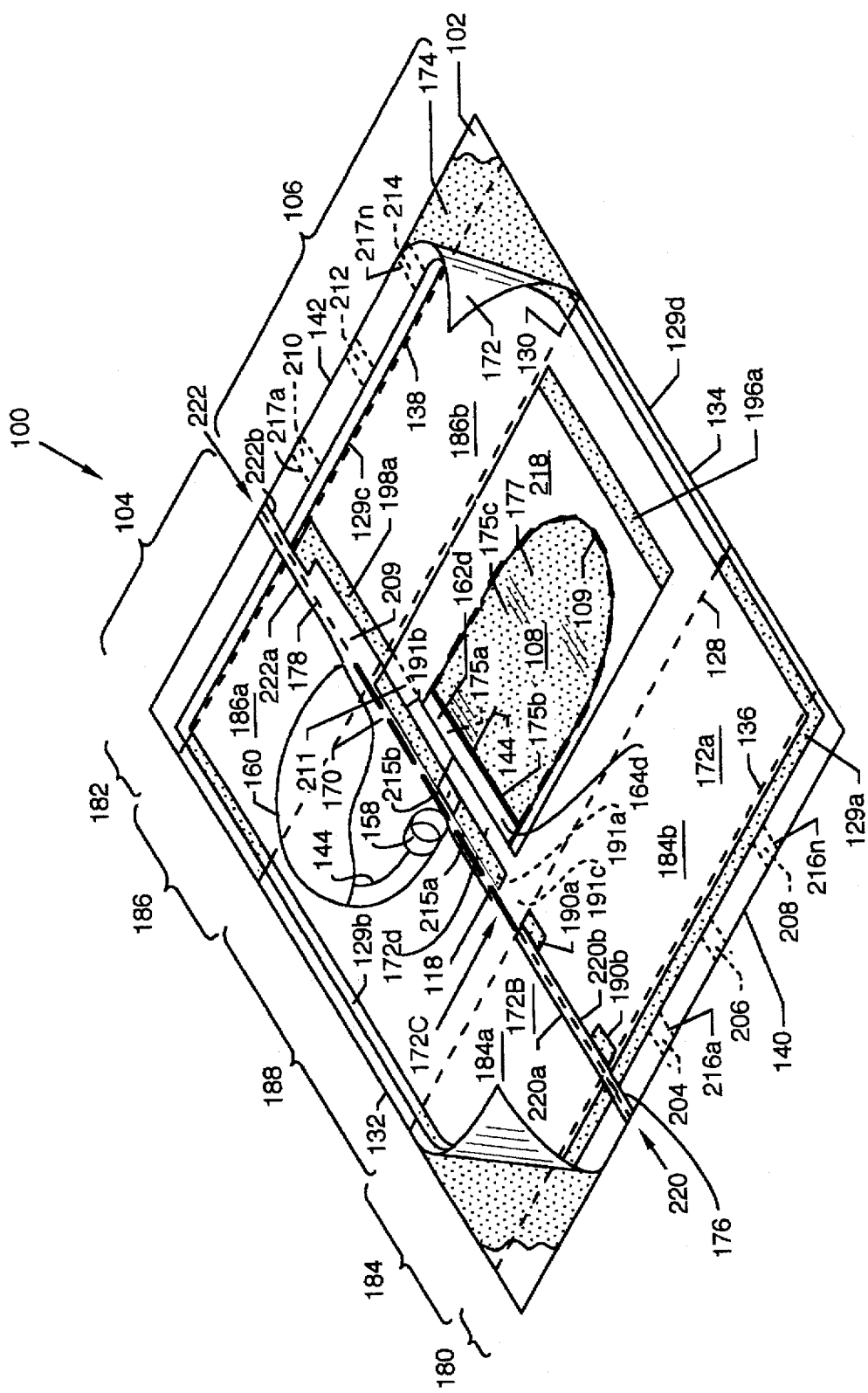
FIG. 10 illustrates the IV bandage with a peel-away backing member adhering to the inner surface of the IV bandage.
Figure 11A:
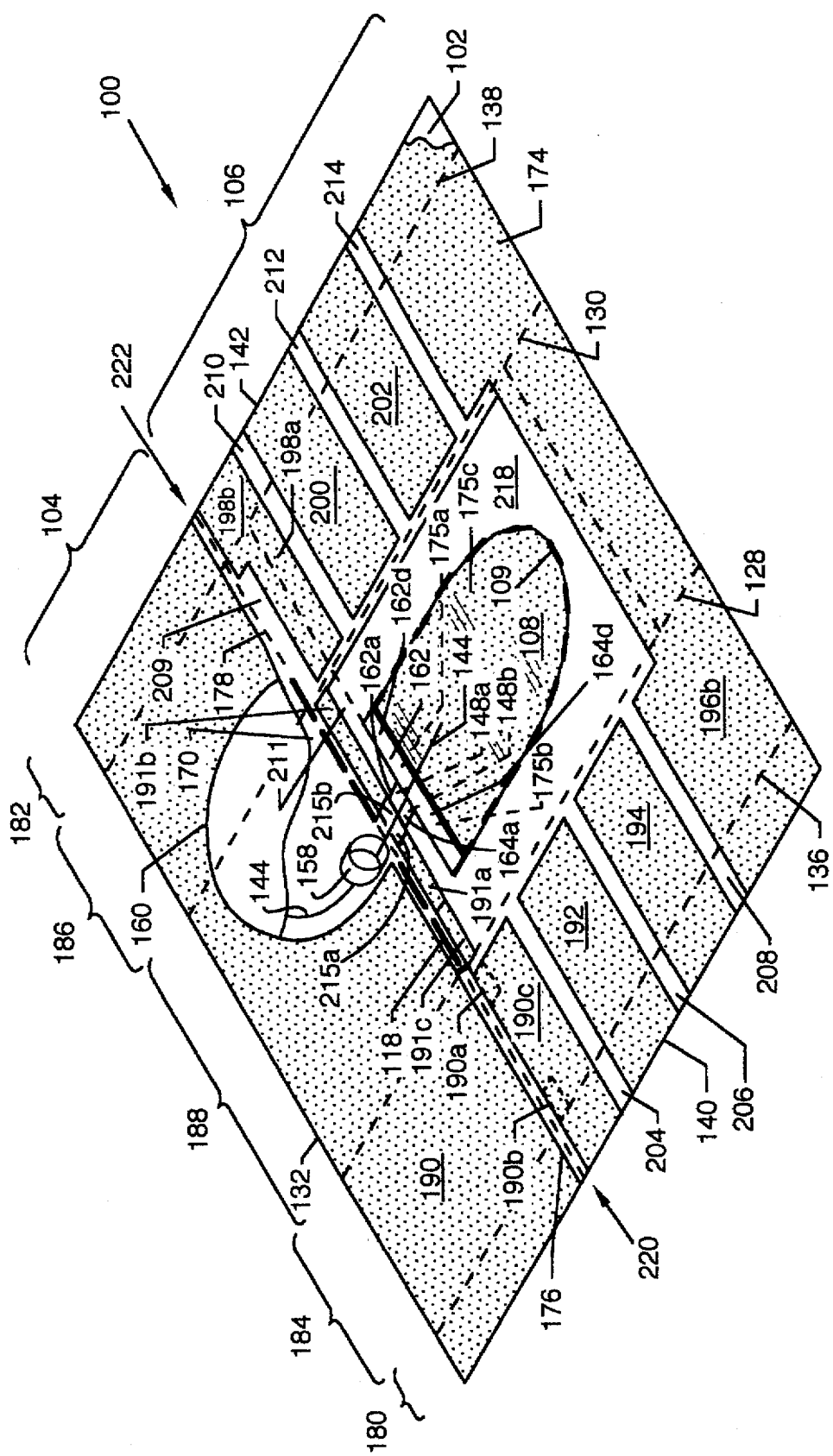
FIG. 11A illustrates the IV bandage with the peel-away backing member removed.

FIGS. 10 and 11A illustrate generally perspective views of the skin application side of intravenous bandage 100 in an unfolded position, all numerals corresponding to elements previously described. FIG. 10 illustrates IV bandage 100 with a peel-away backing of 172 adhering to the inner surface of the IV bandage. The peel-away backing 172 is subdivided into portions 172A, 172B, 172C and 172D. An essentially U-shaped portion 172A aligns over the majority of the dressing membrane portion 106, along edge 134 and portions of edges 140 and 142 leaving the area over and around the dressing membrane 108 and other portions uncovered. Peel-away backing portion 172B aligns between edge 132 and the line formed by frangible perforation 176, fold line 118, and frangible perforation 178, but does not cover pocket 160. Peel-away backing portion 172C is a narrow element connecting portions 172A and 172B across fold line 118. Portion 172C aligns along the inner side of fold line 128. Peel-away backing portion 172D extends centrally from near the region of neck portion 172C to protect one piece removable backing portions 164a and 162a, illustrated in FIG. 11A, from adhesive area 198a upon bandage folding. FIG. 11A illustrates the IV bandage 100 with the protective backing 172A–172D removed. The IV bandage 100 is constructed about a pliable and flexible base material 102, a semi-planar object such as plastic or other such materials known in the art. The base material 102 is transparent in the region of transparent dressing membrane 108. The IV bandage 100 in general is divided into continuous and adjacent pocket securement 104 and dressing membrane 106 portions the same as intravenous bandage 10. Central to the IV bandage 100 and also to the dressing membrane portion 106 is a transparent dressing membrane 108 through which inspection of the skin puncture site can be made after application of the IV bandage 100. Transparent dressing membrane 108 in general resembles a rectangular member, one end of which draws to a point 109. Pocket 160 having an opening 170 fashioned of suitable material, aligns along fold line 118 and a small portion of frangible line 178 and about the pocket securement portion 104 of the IV bandage 100 for accommodation of a fluid administration line. Edges 140 and 142 align between the ends of left and right edges 132 and 134. Peel-away backing member 172 is provided to protect defined areas of adhesive 174 on the skin contact surface of the base material 102. Fold line 118, illustrated as a heavy dashed line, aligns along the axii of and between the inner ends of the frangible perforations 176 and 178. The IV bandage 100 is folded during the manufacturing process about fold lines 128, 130, 136 and 138 to form a complete IV bandage 100 in sterile form such as illustrated in FIG. 8. Pliable and bendable housing members 110, 112 and 114, although expanded in FIG. 8 for illustration, assume a nearly flat profile when not in use.

Adhesive areas of separable and partible adhesive align along and about or in close proximity to the outside edges of the peel-away backing 172 and at the juncture of backing to itself where fold lines 136 and 138 meet to secure planar members as described herein. A continuous sealing strip consisting of sealing strip areas 129a–129d aligns as follows: sealing strip area 129a aligns on the peel-away backing in close proximity to fold line 136, sealing strip area 129b aligns on the peel-away backing 172 in close proximity to edge 132. Sealing strip area 129c aligns on the peel-away backing 172 in close proximity to fold line 138, and sealing strip area 129d aligns on the peel-away backing 172 in close proximity to the edge 134. Sealing strip area 129b is folded about fold lines 128 and 130 into mutual self-contact along and about the edge 132, and sealing strip area 129d, in a like manner, is folded about fold lines 128 and 130 into mutual self-contact along and about the edge 134. At this time sealing strip areas 129a and 129c are brought into contact for mutual contact of planar tab areas 180 and 182. Sealing strip area 129a is adhesive covered. Sealing strip areas 129b and 129d are adhesive covered from their junction with sealing strip area 129a to fold line 128 and between inner fold line 130 and outer fold line 138. The use of adhesives and bandage folding as described provides for a sealed interior, thus maintaining sterility of the pocket securement and membrane portions 104 and 106 respectively.

Planar areas are defined between edges and fold lines during the manufacturing process. Rectangular planar area portions 184 and 186 are the areas between folds 128–136 and 130–138 respectively. The planar area 184 is divided about the frangible perforation 176 to form planar portions 184a and 184b and the planar area 186 is divided about the frangible perforation 178 to form planar portions 186a and 186b. First, folds are made downwardly about outer fold line 136 to form a rectangular planar area tab 180 extending outwardly from the outer fold line 136 to edge 140, and another fold is made downwardly about outer fold line 138 to form a rectangular planar area tab 182 extending outwardly from the outer fold line 138 to edge 142.

Figure 11B:
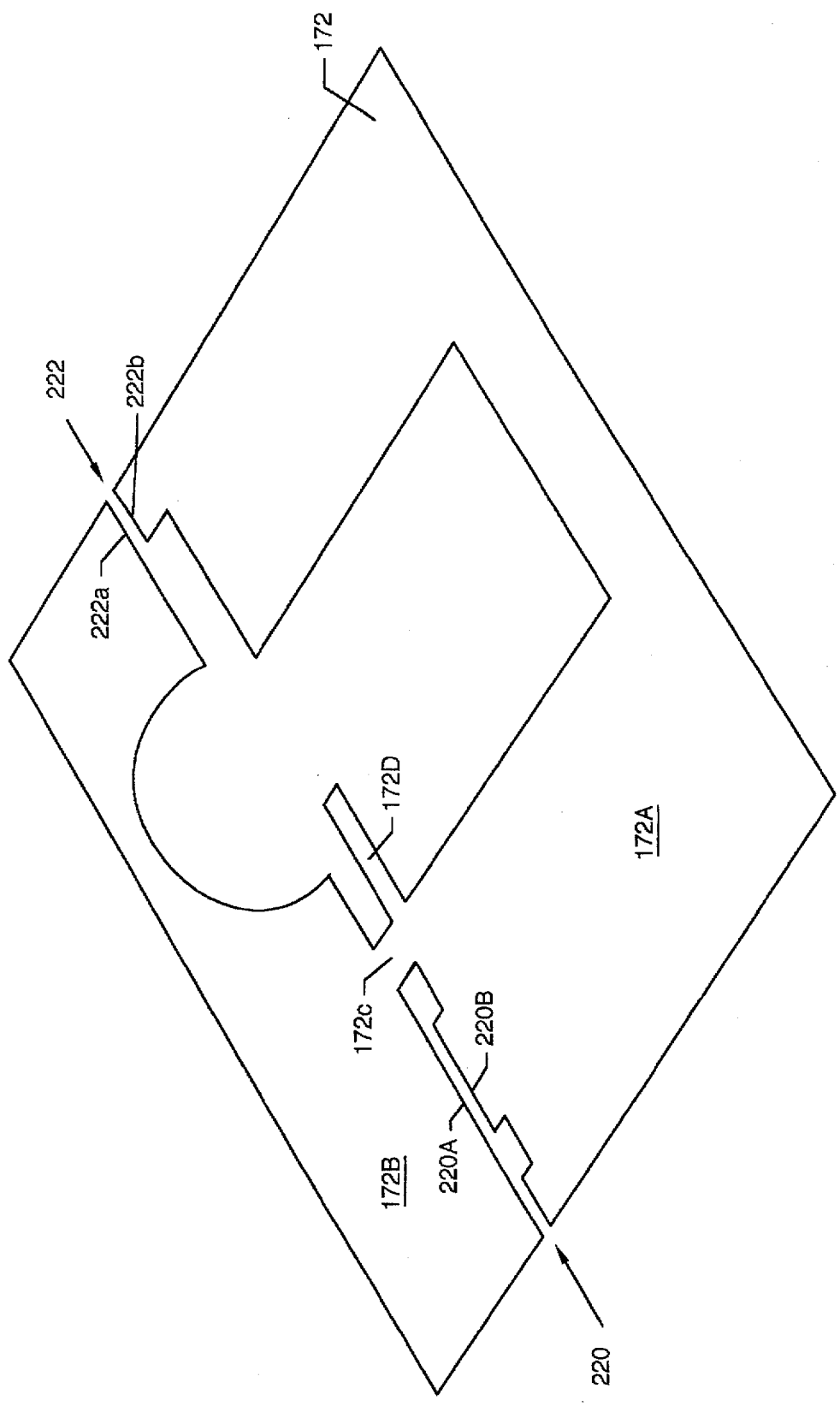
FIG. 11B illustrates an isometric view of the peel-away backing.

Rectangular planar area 188 is bounded by inner fold lines 128 and 130 and portions of edges 132 and 134. Secondly, folds are made upwardly about inner fold lines 128 and 130 to bring rectangular planar area portions 184 and 186 into contact with the rectangular area planar portion 188. As this action occurs, the planar area tabs 180 and 182 are juxtaposed in vertical contact and held together by sealing strip areas 129a and 129c to present as the inverted figure in FIG. 8. The peel-away backing 172 is depicted in FIGS. 10 and 11B. The peel-away backing 172, continuous over large areas of dressing membrane portion 106 and pocket securement portion 104, is provided to protect defined areas of adhesive 174 located on the skin contact surface of the base material 102. Voids in peel-away backing 172 expose adhesive 174 in areas 190a, 190b, 191a, 191b, 196a and 198a. Upon folding, exposed adhesive areas adjacent to frangible perforations 176 and 178 and fold line 118 contact either areas of backing 172 or adhesive-free areas of base 102. The adhesive contacts preserve the sterile isolation of the dressing membrane portion 106 after the opening of the pocket securement portion 104 and separation of frangible perforations 176 and 178. Upon folding by the manufacturer, the following relationships result along the right-hand side of frangible perforation 176, fold line 118, and frangible perforation 178, dividing the pocket securement portion 104 and dressing membrane portion 106 portions of bandage 100. Adhesive area 190a aligning along the dressing membrane portion 106 side of frangible perforation 176 and along the outer side of fold line 128, upon bandage folding contacts peel-away backing portion 172C. Adhesive area 190b aligning along the dressing membrane portion 106 side of frangible perforation 176 and along inner side of the fold line 136, upon bandage folding contacts adhesive-free area 215a. Adhesive area 191a aligns along the dressing membrane portion 106 side of fold line 118 between adhesive-free space 215a and the inner margin of peel-away backing narrow neck portion 172C. Upon bandage folding, adhesive area 191a contacts peel-away backing portion 172A between adhesive areas 190b and 190a. Adhesive area 191a aligns along the dressing membrane portion 106 side of fold line 118 between adhesive-free space 215b and fold line 130. The base of L-shaped adhesive area 198a aligns at the intersection of frangible perforation 178 and fold line 138. Adhesive area 198a aligns between adhesive-free area 209 and adhesive area 198b. Upon bandage folding, adhesive area 191b contacts adhesive-free area 209. Adhesive area 198a, upon bandage folding, contacts the central portion of the peel-away backing portion 172D and adhesive-free areas 215b and 211. Adhesive-free area 211 extends between inner fold line 130 and horizontal backing member 162a and adjacent to adhesive area 191b.

Adhesive area 196a aligns along the right end of rectangular space 218 between fold line 130 and the inner margin of peel-away backing lying parallel to fold line 128. Exposed adhesive areas 196a and 198a secure the fluid administration line when dressing membrane portion 106 is opened and laid down on the skin, near entry to bandage 100, and near entry to pocket 160, respectively.

Bandage 100 adhesive areas covered by peel-away backing 172 are described as follows (see FIG. 11A). Adhesive area 190 aligns along edge 132 and along a portion of edges 140 and 142 but does not include the adhesive covering on the pocket 160 and is essentially L-shaped. The L-shaped end of the adhesive area 190c aligning along the outer edge 140 extends partially on to the dressing membrane portion 106. The adhesive area 191c aligns along fold line 118 beneath neck portion 172C of the peel-away backing. Rectangular adhesive areas 192 and 194 align along edge 140 in between one end of adhesive area 196b and one end of adhesive member 190c. L-shaped adhesive area 198b and rectangular adhesive areas 200 and 202 align along edge 142 and between one end of adhesive area 196b and one inner end of L-shaped adhesive area 190c.

Adhesive-free areas 204, 206, and 208 are located between adhesive areas 190c, 192, 194 and 196b, and adhesive-free areas 209, 210, 212 and 214 are located between adhesive areas 190c, 198a, 198b, 200, 202, and 196b. Areas 204, 206, 208, 210, 212, and 214 intersect a rectangular area 218 in which is positioned a dressing membrane 108. Adhesive-free areas 204, 206, 208, 210, 212 and 214 ventilate the space between the dressing membrane 108 and the base material 102. The adhesive areas 216a–216n on the side of peel-away backing 172 facing base material 102 extends inwardly from the edge 140 in sealing alignment with the outer ends of the adhesive-free areas 204, 206 and 208 respectively to provide for sterile sealing. Similarly, adhesive areas 217a–217n also on peel-away backing portion 172A extend inwardly from the edge 142 in sealing alignment with the outer ends of adhesive-free areas 210, 212 and 214 to provide for sterile sealing. An alternate method of maintaining sterility of the adhesive-free areas 204–214 would be to coat the edges 140 and 142 where peel-away backing 172 and base 102 align with a thin frangible film (see FIG. 10).

Dressing membrane adhesive 177 covering the skin contact side of dressing membrane 108 is divided into adhesive areas 175a–175c. Adhesive area 175c comes in contact with opposing planar areas 184b and 186b of the peel-away backing member 172A as opposing planar areas 184b and 186b are folded about inner fold lines 128 and 130 during manufacturing. Dressing membrane adhesive areas 175a–175b are backed by one piece removable backing member 124 portions 164d and 162d.

Frangible perforation 176 aligns through the base material 102 perpendicularly between the edge 140 and inner fold line 128 and abuts slit 220 in the peel-away protective backing 172 have edges 220a and 220b and, in a like and similar fashion, frangible perforation 178 aligns through the base material 102 perpendicularly between the edge 142 and inner fold line 130 and abuts slit 222 in the peel-away protective backing 172 have edges 222a and 222b.

FIG. 11B illustrates an isometric view of the peel-away backing 172 which overlies the base material 102, all numerals corresponding to elements previously described.

FIG. 12, where all numerals correspond to those elements previously described, illustrates a fluid administration line 230, the end of which has first been passed through capture loop 158, with, secondly, the portion just proximal to loop 158 having been inserted into pocket 160. The distal tubing end 232 can include a cover 235. To achieve the form illustrated in FIG. 12, IV bandage 100 is manipulated in a fashion similar to that outlined for IV bandage 10 in the discussion accompanying FIG. 3. The IV bandage 100 is then inverted and attached to an intravenous cannula in the same manner as that outlined for IV bandage 10 in the discussion accompanying FIG. 5. IV bandage 100 dressing membrane portion 106 is then opened in a fashion similar to that outlined in the discussion accompanying FIG. 6 and applied to the cannula hub. Next, backing 172 is stripped away beginning at 222b and continuing in a circular fashion. In succession, adhesive areas 198b, 200, 202, 196b, 194, 192 and 190c are exposed and pressed into adhesive contact with the skin (see FIG. 11A for adhesive areas). A cross section side view of bandage 100 at this stage of use presents, as in FIG. 13, a view through the major, intermediate and minor housing members 110, 112 and 114. The pocketed loop of the fluid administration line 230 is in alignment with the arcular slit 144 underlying the major housing member 110 (see FIG. 15). The distal end of fluid administration line 230 is in alignment with the lower regions of the one piece removable backing member 124 where it brackets either side of slit 144 (see FIG. 16 cross sectional view through intermediate housing member 114).

Figure 13:
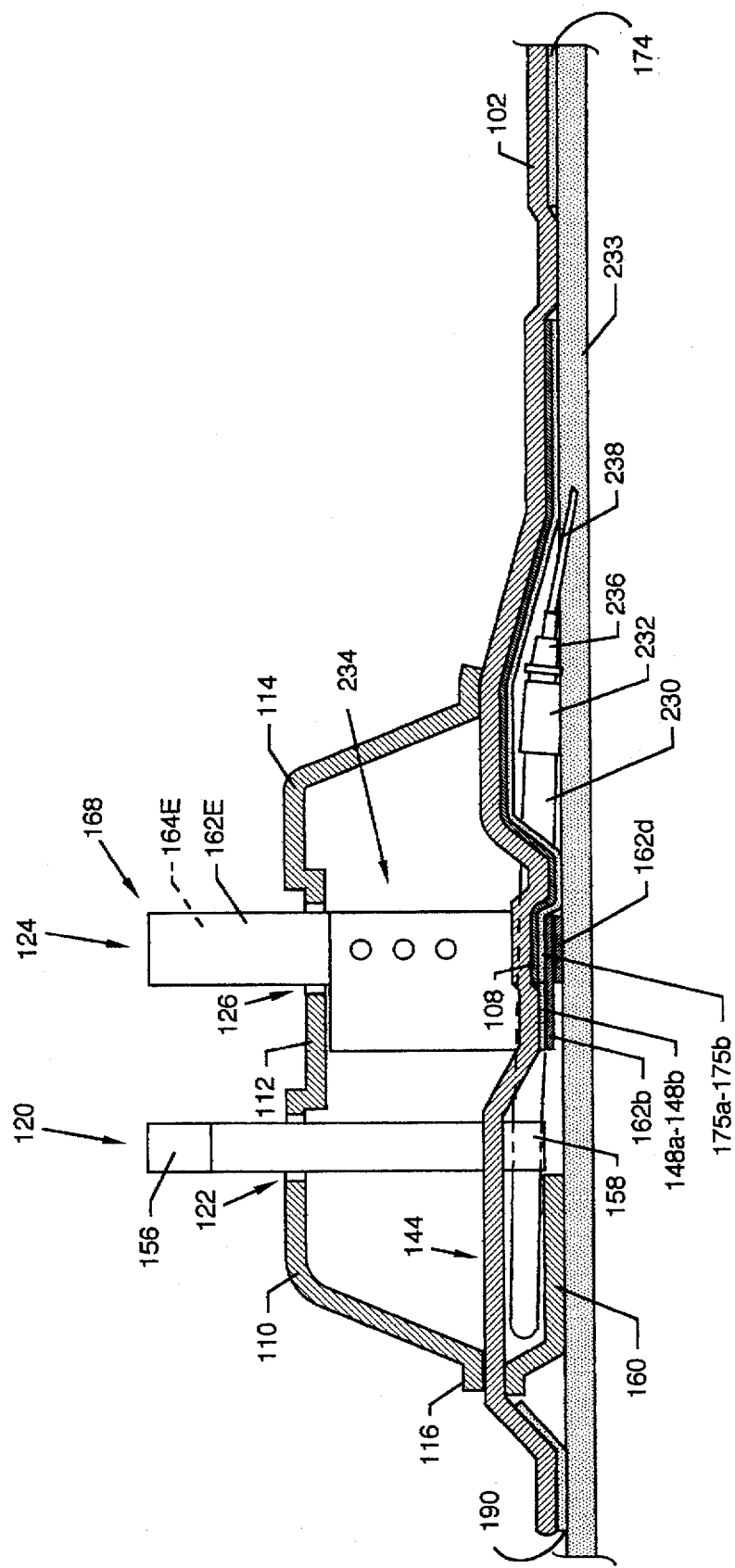
FIG. 13 illustrates a cross sectional view of the major, intermediate and minor housing members where the capture loop is engaging the fluid administration line.
Figure 14:
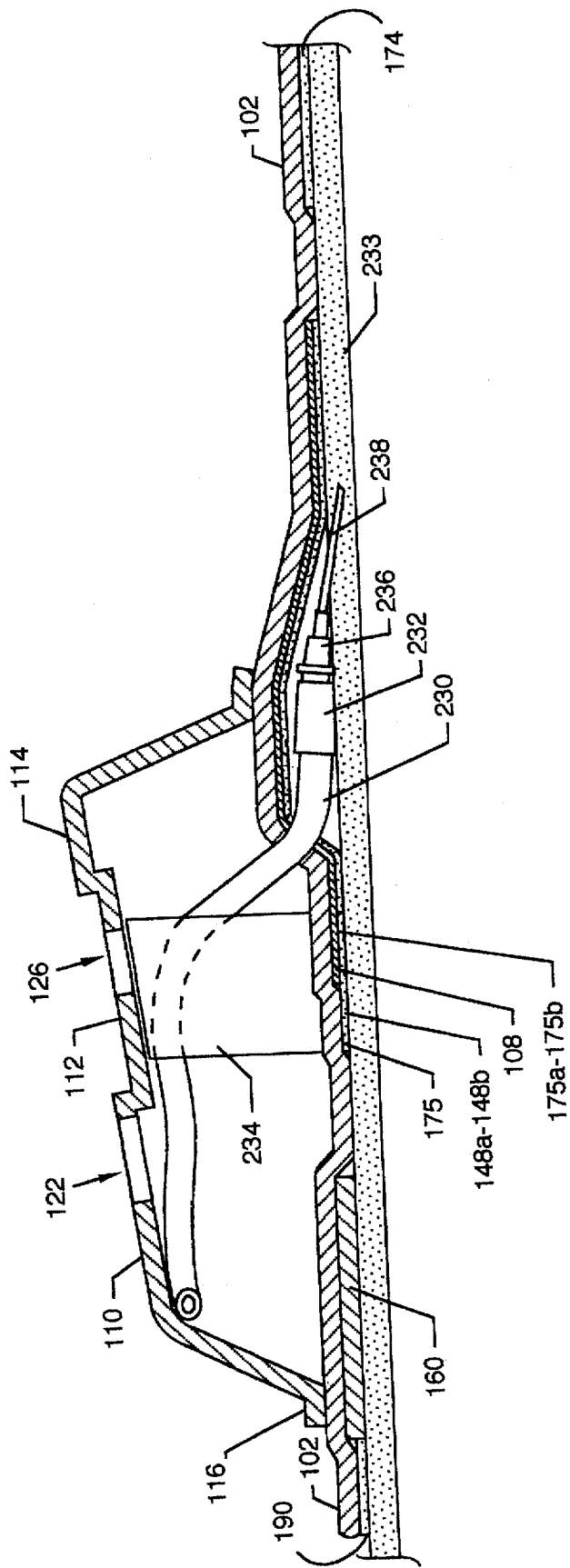
FIG. 14 illustrates the fluid administration line elevated to the upper regions of the housing members and in full engagement of and supported by the umbilicus.
Figure 15:
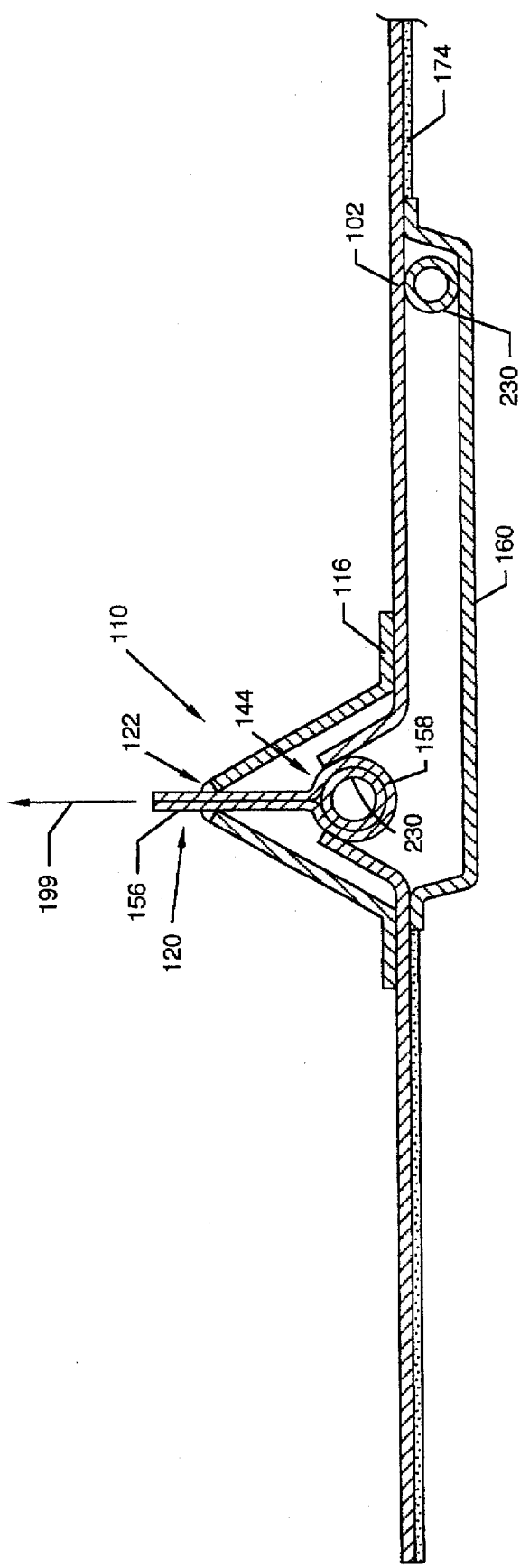
FIG. 15 illustrates a vertical cross section through the major housing member in the area of the capture loop prior to fully raising the fluid administration tube with the capture loop.

Next, as illustrated with cross sectional side views in FIGS. 13, 14 and 15, the tab portion 156 of the capture loop 120 is lifted upward through slits 122 and 144 to raise the fluid administration line 230 through slit 144 into the upper regions of major, intermediate, and minor housing members 110, 112 and 114. Fluid administration line 230 is thereby elevated and positioned between vertical portions 162e and 164e of one piece removable backing member 124, as illustrated in FIG. 16B. The base material 102 overlying adhesive areas 175a and 175b and 148a and 148b is depressed with the thumb and index finger of one hand as the other hand removes one piece removable backing member 124 by pulling up double-layered tab 168 revealing in succession the adhesive areas 175a and 175b, 148a and 148b, 167a and 167b, as shown in FIGS. 9 and 17. Digital pressure bonds; (1) the left-hand margin of dressing membrane 108 (adhesive areas 175a and 175b) to skin; (2) the left and right walls of the intermediate housing member 112 (portions of adhesive areas 167a and 167b) to each other to form umbilicus 234; and (3) portions of left and right walls of intermediate housing member 112 (portions of adhesive areas 167a and 167b) circumferentially to fluid administration line 230.

FIG. 14 illustrates a side view of positioning of the fluid administration line 230 into the major, intermediate and minor housing members 110, 112, 114, and the securing of the fluid administration line 230 to the skin 233 by an umbilicus 234, all numerals corresponding to elements previously described. Slit 144 is closed at the left margin of dressing membrane 108. This, together with sealing of the circumference of dressing membrane 108 and closure of the opening into the minor housing 114 through the intermediate housing 112, protectively isolates the site of cannula entry into the skin from the environment.

Umbilication steps are again described, with reference to cross sectional illustrations as follows: FIG. 16A illustrates a vertical cross section through the intermediate housing member 112 in the region of the one piece removable backing member 124, just subsequent to the inclusion therein of the fluid administration line 230, all numerals corresponding to elements previously described. Positioning of the fluid administration line 230 into the intermediate and minor housing members 112 and 114 forces a portion of the dressing membrane 108 and base material 102 apart along slit 144. The one piece removable backing portions 162d and 164d are placed in skin contact as illustrated in FIGS. 16A and 16B. After raising the fluid administration line 230 with capture loop 120 into the upper regions of the major housing member 110, intermediate housing member 112, as illustrated in FIG. 16B, and the minor housing member 114, one piece removable backing member 124 is pulled upward as indicated by arrow 201 to disengage and remove the planar backing areas 162b and 164b, the ends of which are double-backed upon themselves, from and to reveal the adhesive areas 175a and 175b on the underside of the membrane 108, adhesive areas 148a and 148b, as illustrated in FIG. 9, on the underside of base material 102 and adhesive areas 167a and 167b on the inner aspect of the walls of the intermediate housing member 112. The one piece removable backing member 124 being a flexible, bendable, and pliable material is removed through the slit 126 at the top of the intermediate housing member 112 while the fluid administration line 230 is kept in position in the upper region of the intermediate housing member 112 by thumb and index finger of the operators other hand. Digital pressure is simultaneously applied to vertical and horizontal portions of intermediate housing member 112. The underlying exposed adhesive areas 167a, 167b, 148a, 148b, 175a and 175b produce full circumferential adhesion of intermediate housing member 112 right and left walls to IV tubing 230, to each other and adhesion of the base of intermediate housing number 112 (via base material 102 and transparent membrane 108) to skin, as illustrated in FIG. 17. Slit 144 is closed at margin of dressing membrane 108. This closure together with sealing of the circumference of dressing membrane 108 protectively isolates the site of cannula entry into the skin from the environment.

Figure 18:
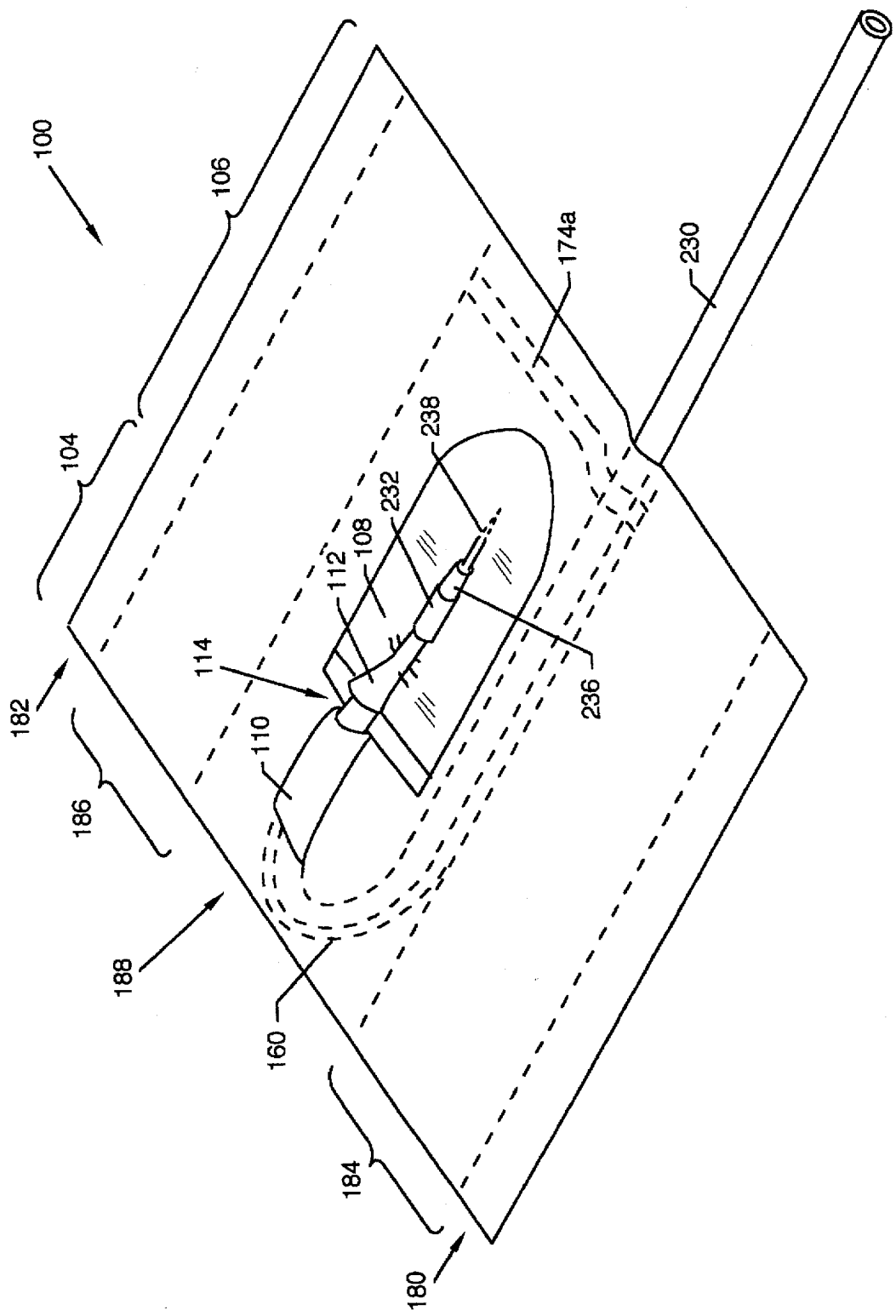
FIG. 18 illustrates the IV bandage in its final use position.

FIG. 18 illustrates the IV bandage 100 in its final use position, including IV tube 230, hub 236 and cannula 238 where all numerals corresponding to those elements previously described.

DETAILED DESCRIPTION OF THE SECOND ALTERNATIVE EMBODIMENT

Figure 19:
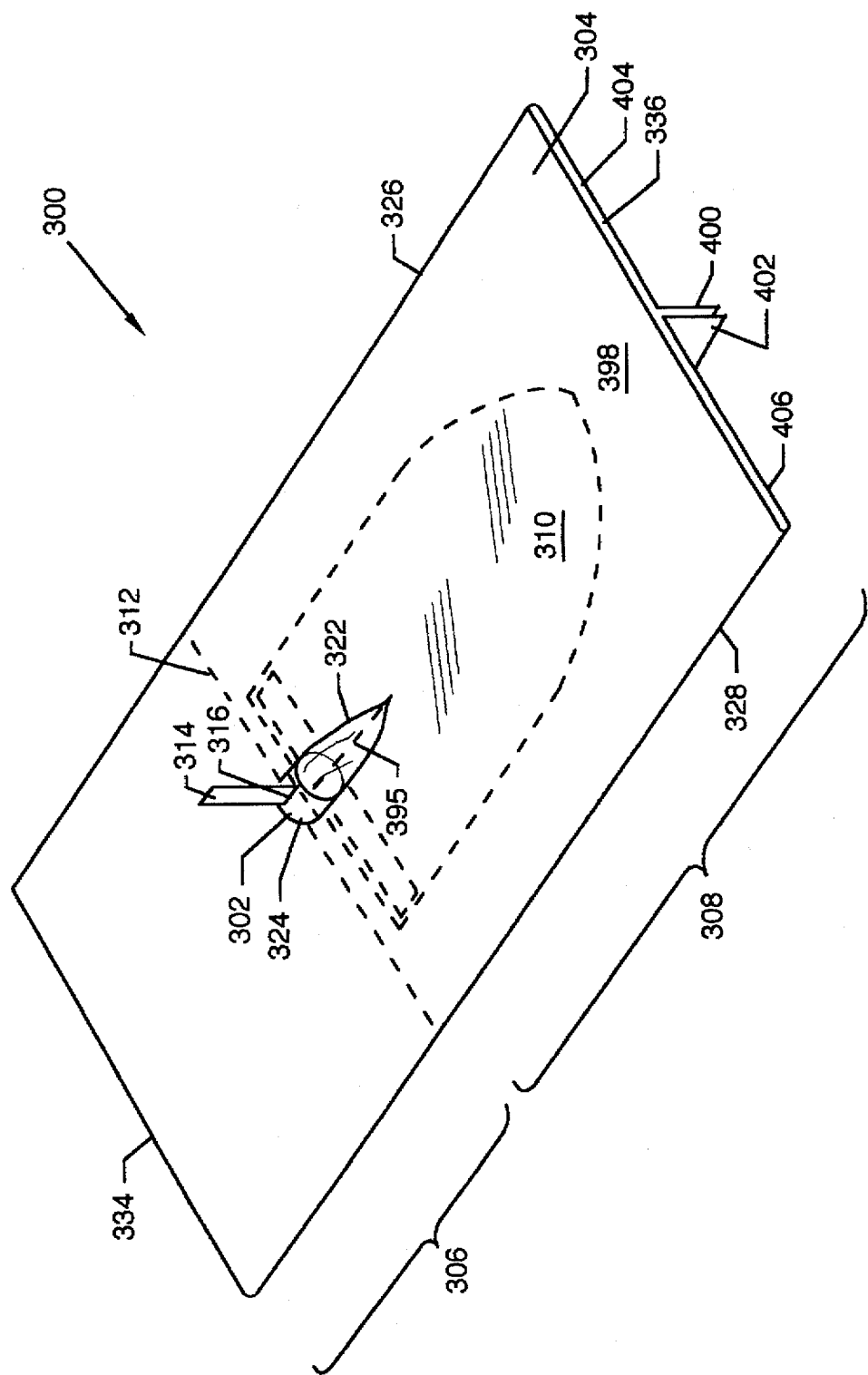
FIG. 19, a second alternative embodiment, the subject of which is also included in FIGS. 20 through 29, illustrates an isometric view of a bandage for anchoring and securing a plurality of indwelling tubes, lines and like appliances to the skin.

FIG. 19, a second alternative embodiment, illustrates an isometric view of a bandage 300 as presented for dressing and anchoring a variety of indwelling tubes, lines or appliances to the skin. As with bandages 10 and 100, bandage 300 conveniently attaches as a handle to tubes, lines or appliances in advance of their connection to patients, is single use and accomplishes both sterile dressing and anchoring functions in a fashion economical of time, motion and materials. The bandage 300 differs with respect to an adhesive lined clip member 302 in which a tube, line or appliance can be secured. As the bandage 300 is secured to the skin, so is the tube, line or appliance via the clip member 302. The skin puncture site is isolated from the environment in a fashion similar to that with intravenous bandages 10 and 100. During the deployment process, protective backing is removed from the inner arcular surfaces and from adjacent flat surfaces of the clip 302 and from adjacent dressing membrane areas to provide for adhesive anchoring and securing of indwelling tubes, lines or appliances.

Figure 26:
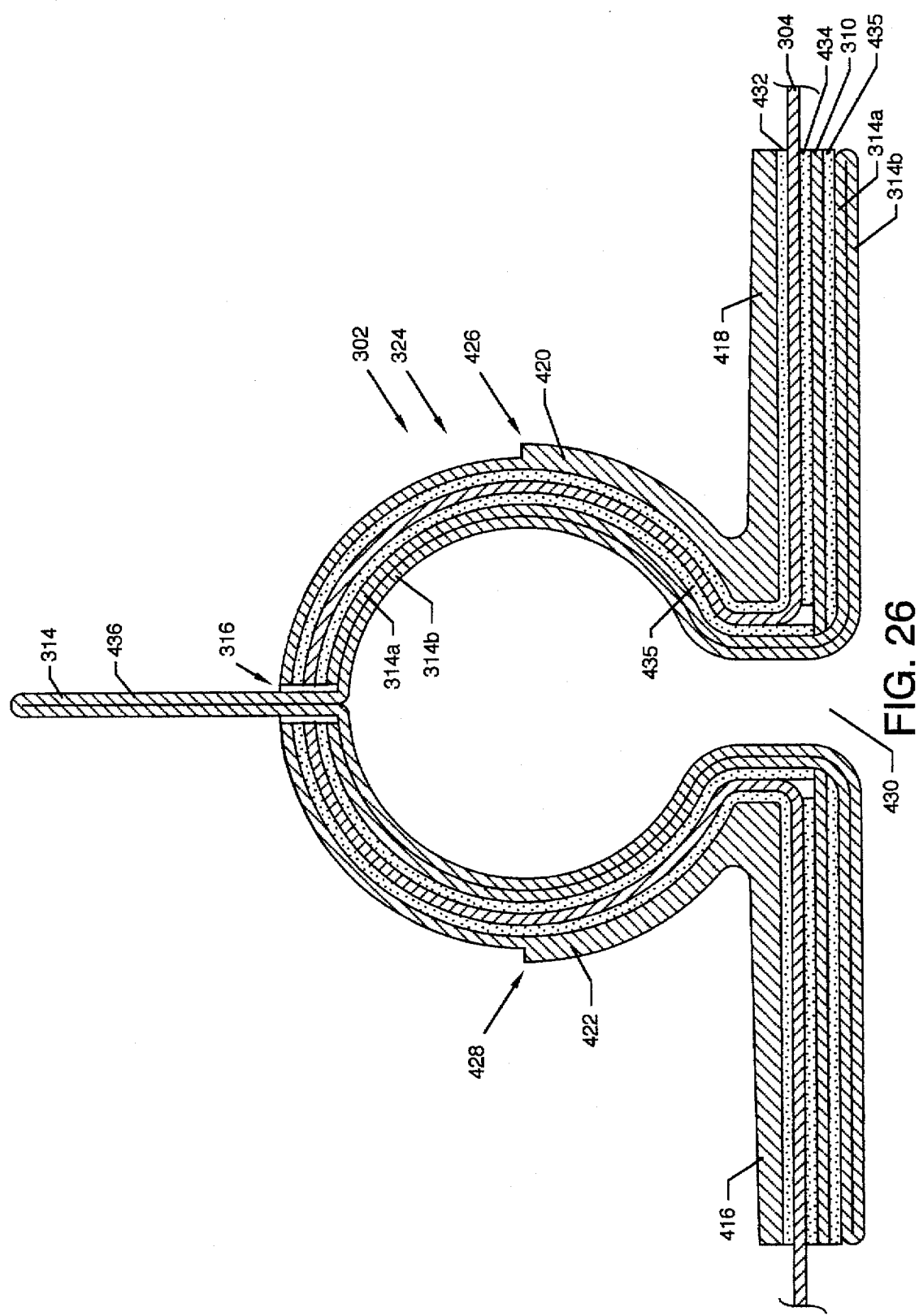
FIG. 26 illustrates a conceptual cross sectional view of the clip in attachment to the base material.

The bandage 300 has a base material 304 which is divided generally into a securement portion 306 and a dressing membrane portion 308. A clear, sterile dressing membrane 310 is located central to the dressing membrane portion 308. The base material 304 overlying the dressing membrane 310 is clear in that region. The securement portion 306 aligns generally to the left of a fold line 312, shown in heavy dashed lines. The dressing membrane portion 308 aligns to the right of the fold line 312. Removable backing strip 314 extends upwardly through a slit 316 in the clip 302 and downwardly into the interior of the clip 302 and continues horizontally along the skin contact surface and flat layered members, including glue 432, base material 304, dressing membrane 310 and adhesive layers 435, as illustrated in FIG. 26. A frangible film (not illustrated) seals, in sterile fashion, the two layers of removable backing strip 314 and the narrow space between it and the margin of slit 316 until use.

Figure 20:
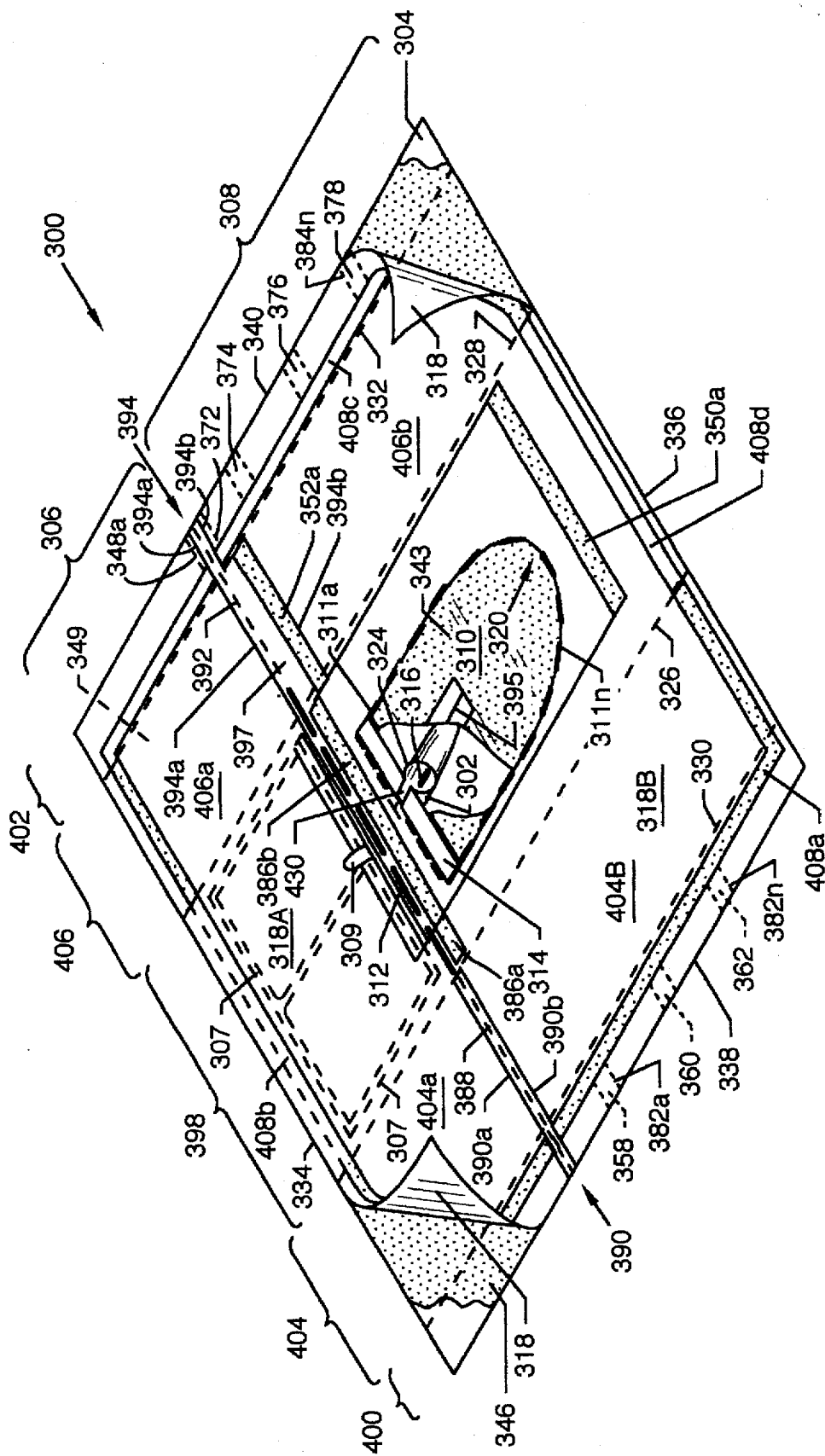
FIG. 20 illustrates the bandage in the unfolded position including a peel-away backing.
Figure 21A:
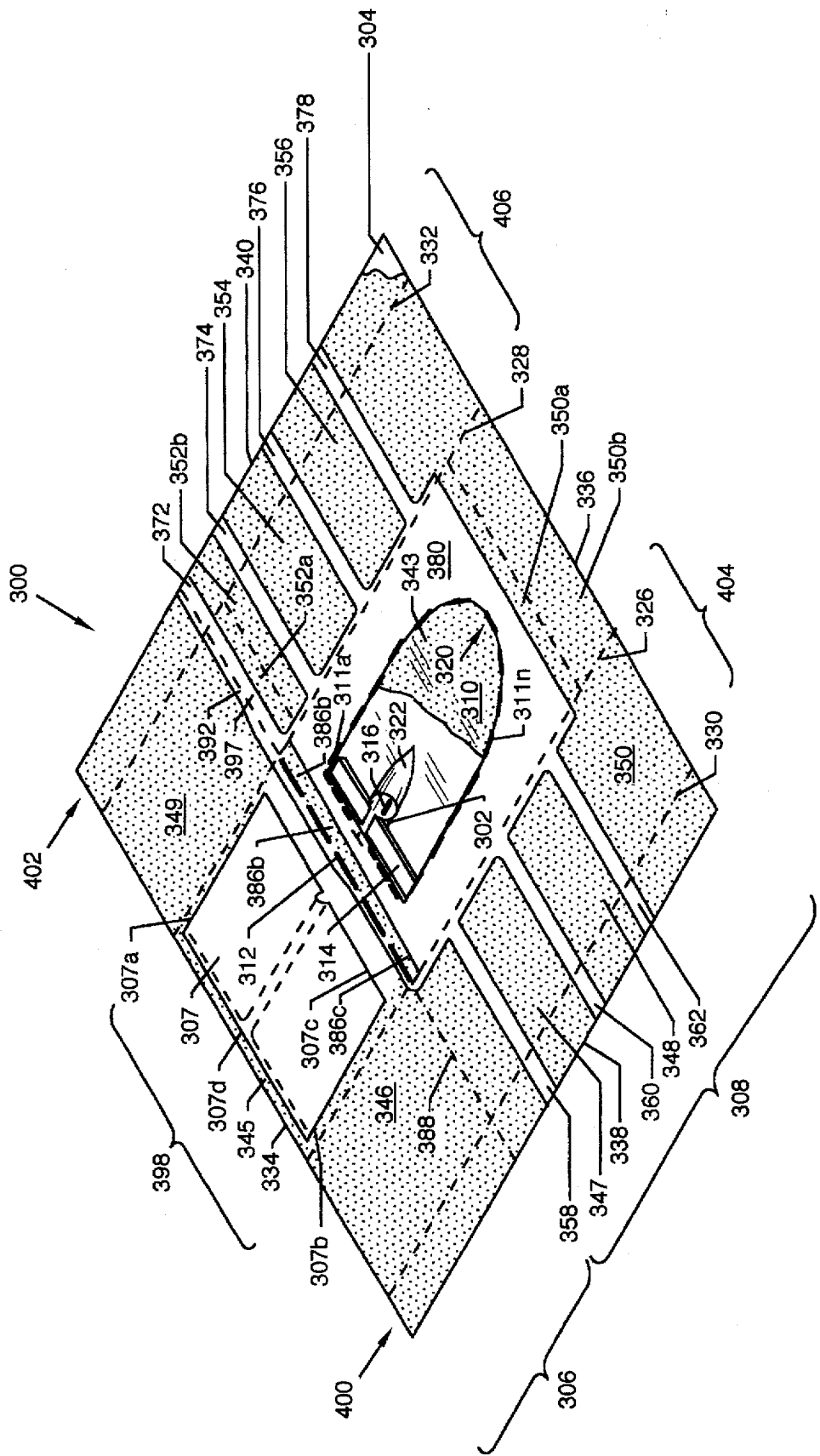
FIG. 21A illustrates the bandage of FIG. 20 with the peel-away backing removed.
Figure 25:
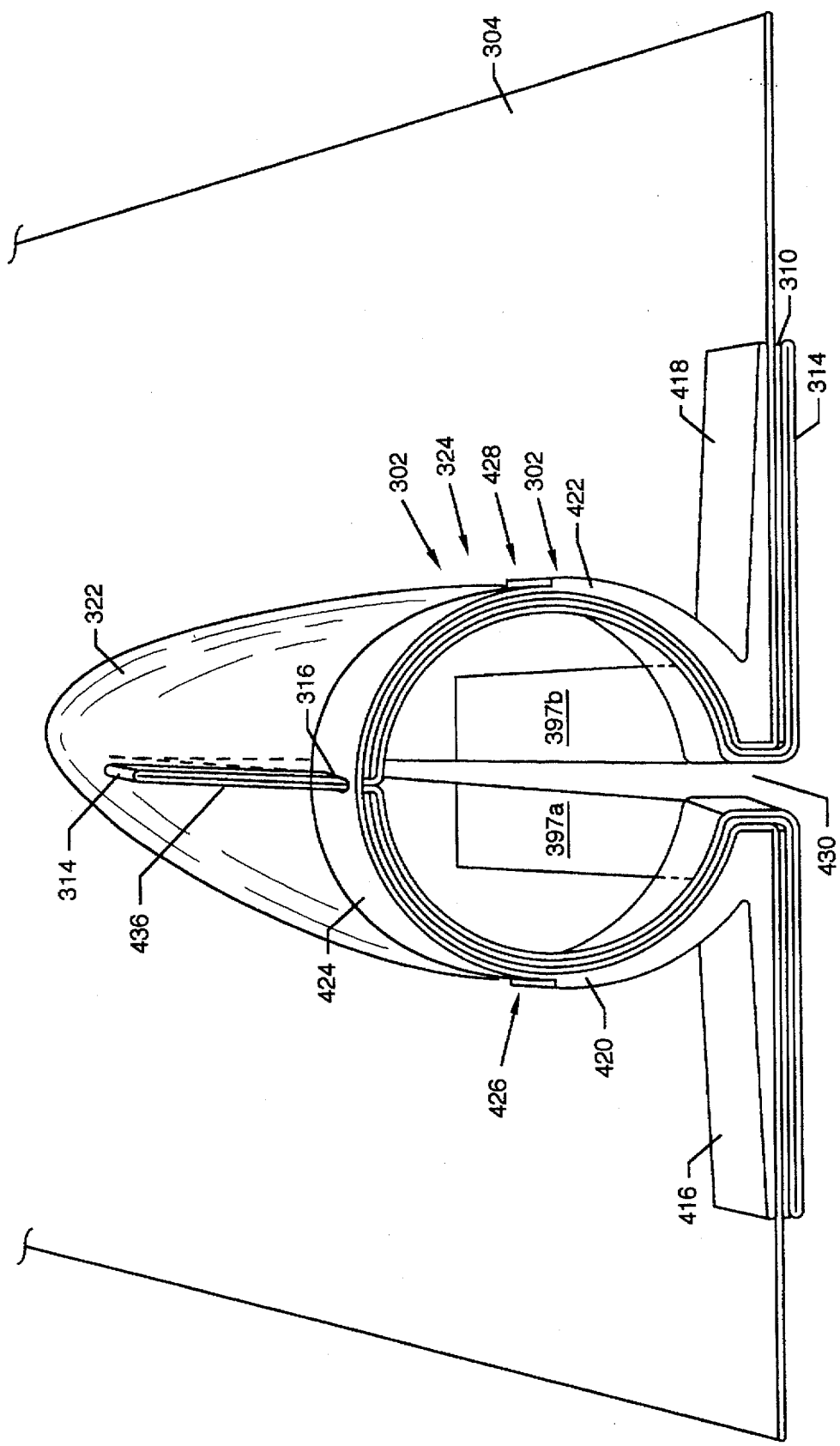
FIG. 25 illustrates the sterile dressing membrane and base material in alignment and securement to the clip.

FIGS. 20 and 21A illustrate isometric views of a bandage 300 in an unfolded position. FIG. 20 illustrates the bandage 300 with a peel-away backing 318 adhering to the inner surface of the bandage 300. FIG. 21A illustrates the bandage 300 with the peel-away backing 318 removed. The bandage 300 is fabricated about a pliable and flexible base material 304 illustrated as a planar object such as plastic or other such material known in the art. The bandage 300 is divided into continuous and adjacent securement and dressing membrane portions 306 and 308. The securement portion 306 secures tubes, lines or appliances to the bandage 300. It is anticipated that for some tubes, lines or appliances, the optimal use of the bandage 300 would include incorporation into securement portion 306 at time of their packaging. Central to the IV bandage 300 and to the dressing membrane portion 308 is a sterile dressing membrane 310. This dressing membrane 310 in general resembles a rectangular member, one end of which draws to a point 320. The dressing membrane 310 protects the skin entry site from moisture and other contaminates. It is breathable, allowing moisture beneath it to evaporate. The skin entry site may be inspected through it and the adjacent overlying transparent base material 304. The dressing membrane 310 is intermittently sealed by a plurality of sealing areas 311a–311n to the flexible base material 304 in a manner to incorporate a plurality of openings between the dressing membrane 310 and the base material 304. The openings ventilate the area between the dressing membrane area 310 and the overlying base material 304. The region of the base material 304 overlying the dressing membrane 310 is also transparent. The clip 302 secures to the base material 304 such as by welding or gluing. The removable backing strip 314 is shown in FIG. 25. The removable backing strip 314 covers the clip tapered base members 416 and 418, (glue layers 432 and 434, base material 304, dressing membrane 310, and adhesive 435 layers intervening) skin contact surfaces and interior arcular surfaces, all of which are adhesive laden. The clip 302 adhesive areas are revealed by removing backing strip 314. The base material 304 includes a shroud expansion 322 connecting and securing to the interior of the circular portion 324 of the clip 302. Longitudinal fold lines are positioned parallel to the longitudinal axis of the IV bandage 300 including factory made inner fold lines 326 and 328 and factory made outer fold lines 330 and 332, each of which intersect left and right edges 334 and 336 of the base material 304. Edges 338 and 340 align between the ends of left and right edges 334 and 336. The peel-away backing member 318, continuous over large areas of dressing membrane portion 308 and securement portion 306, protects defined areas of adhesive 346, 350 and other intermediate adhesive areas located on the inner surface of the base material 304. Peel-away backing member 318 can be subdivided into backing portions 318A and 318B. Backing portion 318A generally aligns between edge 334 and the line formed by frangible perforation 388, fold line 312, and frangible perforation 392. Its two short margins align along edge 338 and edge 340. A securement layer 307 is included for anchoring of tubes, lines or appliances. For examples of bandage 300, intended for end user installation of tubes, lines or appliances with securement portion 306, the left-hand outer margin of peel-away backing portion 318A between fold lines 326 and 328 lies parallel to and between sealing strip area 408b and the left-hand margin of securement layer 307. For examples of bandage 300 intended for manufacturer installation of tubes, lines or appliances within securement portion 306, the left-hand outer margin of peel-away backing portion 318a is contiguous with bandage left edge 334. Securement layer 307 attaches to the inner surface of base material 304 such as by gluing or welding at its two opposing sides or margins 307a and 307b a short distance from and parallel to and central to fold lines 326 and 328. The left and right sides or margins 307c and 307d of the securement layer 307 are not attached to the base material; they lie parallel to and to the right of sealing strip 408b and parallel to and to the left of fold line 312 respectively. The securement layer 307 which secures installed tubes, lines or appliances is faced with securement layer adhesive 303. In examples of bandage 300 intended for user installation of tubes, lines or appliances, the inner surface of the securement layer 307 is faced with a doubled back removable backing layer 305 having a tab 309. The tab 309 extends from near edge 307d between backing layer 305 and opposing base material 304 to emerge at edge 307c.

An essentially U-shaped backing member portion 318B aligns over the majority of the dressing membrane portion 308 along edge 336 and between portions of edges 338 and 340 leaving the area over and around the dressing membrane 310 uncovered. Dressing member adhesive 343 covers the skin contact side of dressing membrane 310. Dressing member adhesive 340 comes in contact with portions of the peel-away backing 318B corresponding to planar areas 404b and 406b upon bandage folding at lines 326 and 328 during manufacturing. Adhesive areas 350a and 350b, portions of adhesive area 350, illustrated in FIG. 21A, align between portions of fold lines 326 and 328 and starting at edge 336 and extending inwardly until meeting with the large adhesive-free space 380. Adhesive strip area 350a is exposed and illustrated in FIG. 20 parallels the central margin of peel-away portion 318B opposite dressing membrane point 320. Peel-away backing portion 318B connects to peel-away backing member 318A via a narrow neck of backing material bridging fold line 312 just central to fold line 326. In FIG. 21A, adhesive area 346 aligns along edge 334 and along a portion of edge 338. In the case of bandage 300 intended for user installation of lines, tubes or appliances within securement portion 306, there is an adhesive-free area 345 of base material 304 between edge 334 and the left margin 307d of securement layer 307 between fold lines 326 and 328. For examples of bandage 300 intended for manufacturer installation of tubes, lines or appliances within securement portion 306, this area 345 of base material 304 would be adhesive covered. The skin contact surface of the securement layer 307 could present with or without adhesive. The L-shaped end of adhesive area 346 extends partially onto the dressing membrane portion 308. Adhesive area 349 aligns along portions of edges 334 and 340. Rectangular adhesive areas 347 and 348 align along edge 338 and between one of the U-shaped ends of adhesive area 350 and one inner end of adhesive area 346. Adhesive areas 352a, 352b, 354 and 356 align along or in close proximity to edge 340 and between one of the ends of the U-shaped adhesive area 350 and adhesive area 349. Accordingly, adhesive-free spaces 358, 360 and 362 are located between adhesive areas 346, 347, 348 and 350 and adhesive-free spaces 372, 374, 376 and 378 are located between adhesive areas 349, 352, 354, 356 and 350. Spaces 358, 360, 362, 372, 374, 376, and 378 intersect an adhesive-free rectangular space 380 surrounding the dressing membrane 310. Spaces 358, 360, 362, 372, 374, 376, 378 and 380 are free of adhesive to allow ventilation from ambient air to the space between the dressing membrane 310 and the base material 304 when applied to the skin. Adhesives areas 382a–382n on the underside of the peel-away backing member 318B extend inwardly from the edge 338 and are in sealing alignment with the outer portions of the adhesive-free areas 358, 360 and 362 respectively to provide for sterile sealing. In a similar fashion, adhesive areas 384a–384n on the underside of the peel-away backing portion 318B extend inwardly from the edge 340 and are in sealing alignment with the outer portion of the adhesive-free areas 372, 374, 376, and 378 respectively to provide for sterile sealing. Exposed adhesive area portions 350a, 386a and 386b align perpendicular to opposing end areas of the dressing membrane 310. Frangible perforation 388 through the base material 304 aligns perpendicularly between edge 338 and inner fold line 326 and adjacent to slit 390 in the peel-away backing 318 having edges 390a and 390b. Frangible perforation 392 aligns perpendicularly between edge 340 and inner fold line 328 through the base material 304 and adjacent to a slit 394 in the peel-away backing 318 having edges 394a and 394b. Exposed adhesive area 352a lies between adhesive-free area 397 and the inner margins of peel-away backing portion 318B as illustrated in FIG. 20. The fold line 312 illustrated as a heavy dashed line, aligns along the axis of and between the inner ends of the frangible perforations 388 and 392. The IV bandage 300 is folded during the manufacturing process about fold lines 326, 328, 330 and 332 to form a ready-to-use bandage 300 in sterile form as illustrated in FIG. 19. Planar areas are defined between various edges and fold lines. The planar area 398 between the inner fold lines 326 and 328 is not folded and remains planar. Firstly, folds are made downwardly about outer fold line 330 to form a rectangular planar tab 400 extending outwardly from the outer fold line 330 to the edge 338, and another fold is made about outer fold line 332 to form a rectangular planar area tab 402 extending outwardly from the outer fold line 332 to edge 340. Rectangular planar area portions 404 and 406 are the areas between folds 326 and 330, and 328 and 332 respectively. Secondly, folds are made upwardly about inner fold lines 326 and 328 to bring rectangular planar area portions 404 and 406 into close intimate contact with the planar area 398. As this action occurs the planar area tabs 400 and 402 are juxtaposed in intimate vertical contact and held together by mutual contact of opposing portions of sealing strips 408a and 408c to achieve the form presented, although inverted, in FIG. 19.

Areas of adhesive align along or in close proximity to the outside edges of the peel-away backing 318 and at the juncture of the backing to itself where fold lines 330 and 332 meet to secure planar members as described herein. A continuous sealing strip consisting of sealing strip areas 408a–408d aligns as follows: sealing strip area 408a aligns on the peel-away backing 318 in close proximity to fold line 330. Sealing strip area 408b, in the case of manufacturer installed lines, tubes or appliances, aligns on the peel-away backing 318 in close proximity to edge 334. In the case of bandage 300 intended for user installation of lines, tubes or appliances, sealing strip 408b aligns in close proximity to edge 334, and includes adhesive between sealing strip 408a and fold line 326 on peel-away backing 318A; an adhesive-free area between fold lines 326 and 328, and adhesive from fold line 328 to fold line 332 on peel-away backing 318A. Sealing strip area 408c containing adhesive aligns on the peel-away backing 318 in close proximity to fold line 332. Sealing strip area 408d aligns on the peel-away backing 318 in close proximity to the edge 336. Sealing strip area 408b is folded about fold lines 326 and 328 into mutual self-contact along and about the edge 334 and sealing strip area 408d and in a like manner is folded about fold lines 326 and 328 into mutual self-contact along and about the edge 336. At this time sealing strip areas 408a and 408c are brought into contact for bonding of planar tab areas 400 and 402. Sealing strip area 408a is adhesive covered. Sealing strip areas 408b and 408d are adhesive covered from their junction with adhesive area 408a to inner fold line 326 and between inner fold line 328 and outer fold line 332. Sealing strip area 408c is adhesive free. The use of adhesives and the folding as described provides for a sealed interior thus maintaining sterility of the securement and dressing membrane portions 306 and 308 respectively. Additional sealing of the dressing membrane portion 308 exists to provide and maintain a sterile dressing membrane area environment when the dressing membrane and securement portions 308 and 306 respectively are fractured along and about perforations 388 and 392. As seen in FIG. 20, exposed adhesive area 386b continues as 386a a snort distance towards fold line 326 on the exposed surface of peel-away backing 318 which at that region serves to join portions 318A and 318B. Adhesive area 386c to the right of fold line 312 on base material 304 extends between fold line 326 and adhesive area 386b. In the factory folded position, the peel-away backing 318 edge 390b between inner fold line 326 and outer fold line 330 is in adhesive contact with adhesive area 386a and the left-hand segment of adjacent adhesive area 386b. In the factory folded position the base material adhesive-free area 397 between outer fold line 332 and inner fold line 328 is in adhesive contact with an adjacent segment of adhesive area 386b. The planar area 404 is divided about the frangible perforation 388 to form planar portions 404a and 404b. The planar area 406 is divided about the frangible perforation 392 to form planar portions 406a and 406b.

Figure 21B:
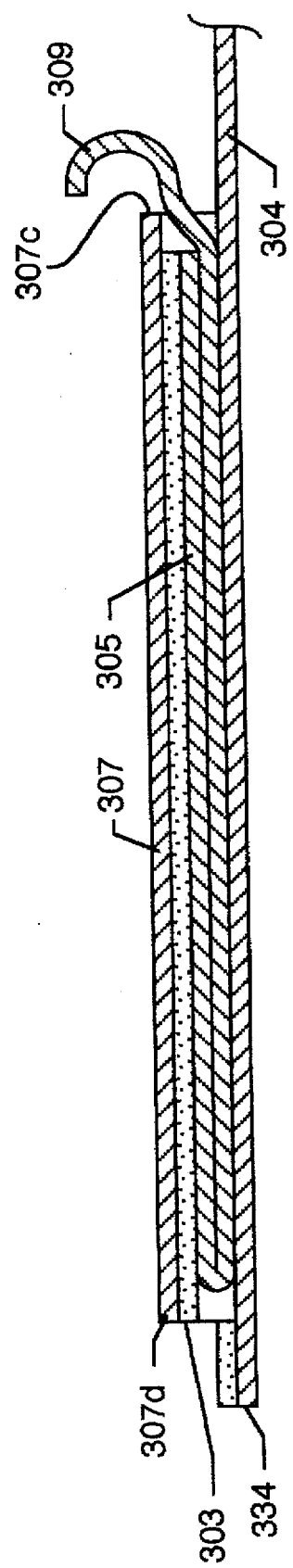
FIG. 21B illustrates a cross sectional view through the securement layer of FIG. 20.

FIG. 21B illustrates a cross sectional view through the securement layer 307 of FIG. 20 where all numerals correspond to those elements previously described. Adhesive 303 coats the underside of the securement layer 307. A doubled back removable backing layer 305 having a tab 309 allows for tubes, lines or appliances or the like to be inserted and positioned between the securement layer 307 and the base material 304 without contacting the adhesive 303 which is covered by the doubled back removable backing layer 305. Upon proper tube, line or appliance positioning, tab 309 is grasped and pressure is exerted to remove the removable backing layer 305 to expose the adhesive 303. Downward pressure is then exerted on the securement layer 307 to cause the adhesive 303 to contact and anchor the tubes, lines or appliances between the adhesive covered securement layer 307 and the base material 304.

Figure 22:
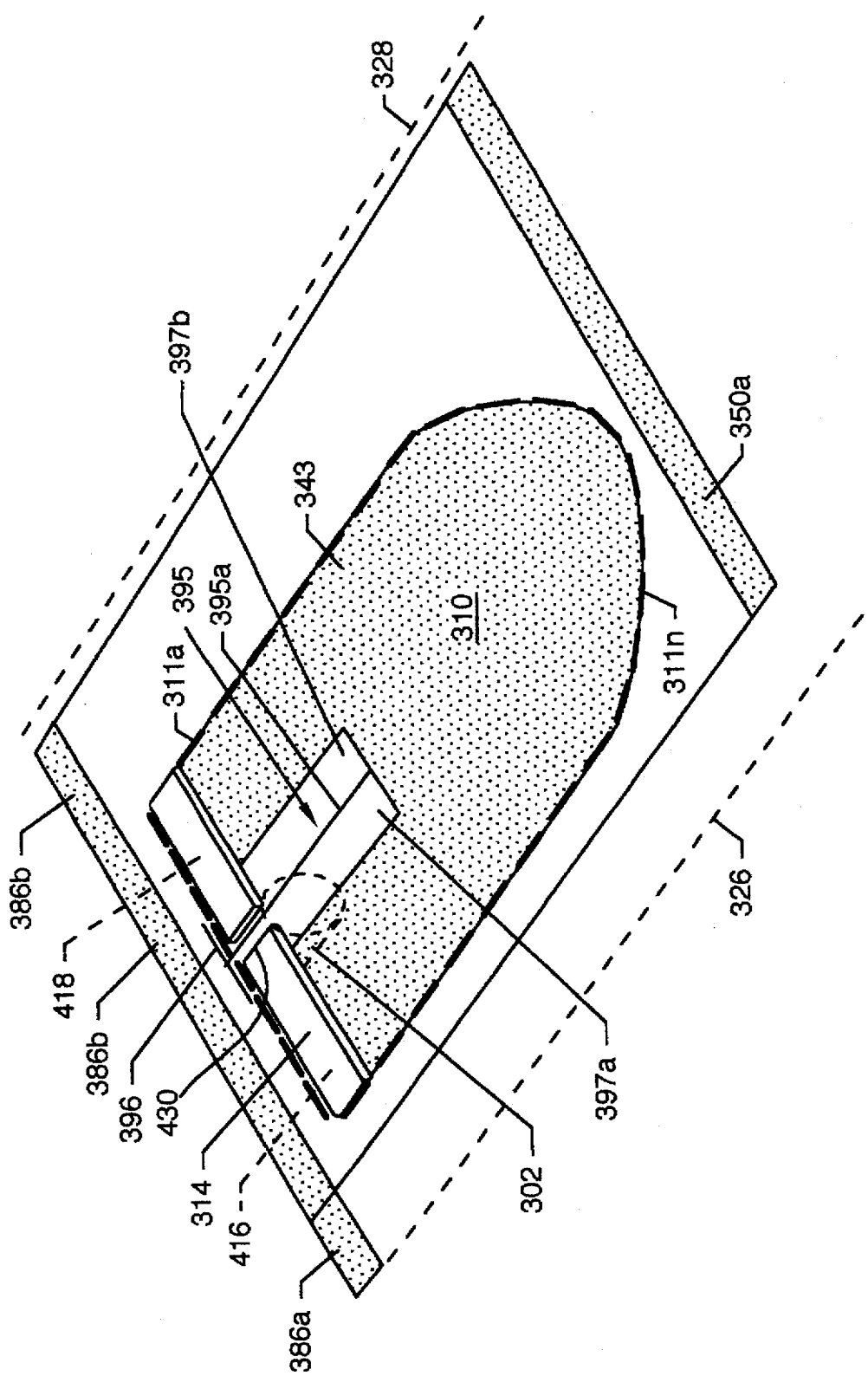
FIG. 22 illustrates the membrane dressing and its associated members.

As illustrated in FIG. 22, dressing membrane slit 395 meets base material 304 frangible perforation 396 perpendicularly at its midpoint. Adhesive free areas 397a and 397b adjacent to dressing membrane slit 395 allow for unimpeded passage of tubes, lines or appliances through the dressing membrane 310. Together, slit 395 and frangible perforation 396 allow for flexion of base material 304 and dressing membrane 310, thus allowing the radius of the clip 302 to be bendably enlarged for insertion of tubes, lines or appliances into the center of the clip 302.

Figure 23:
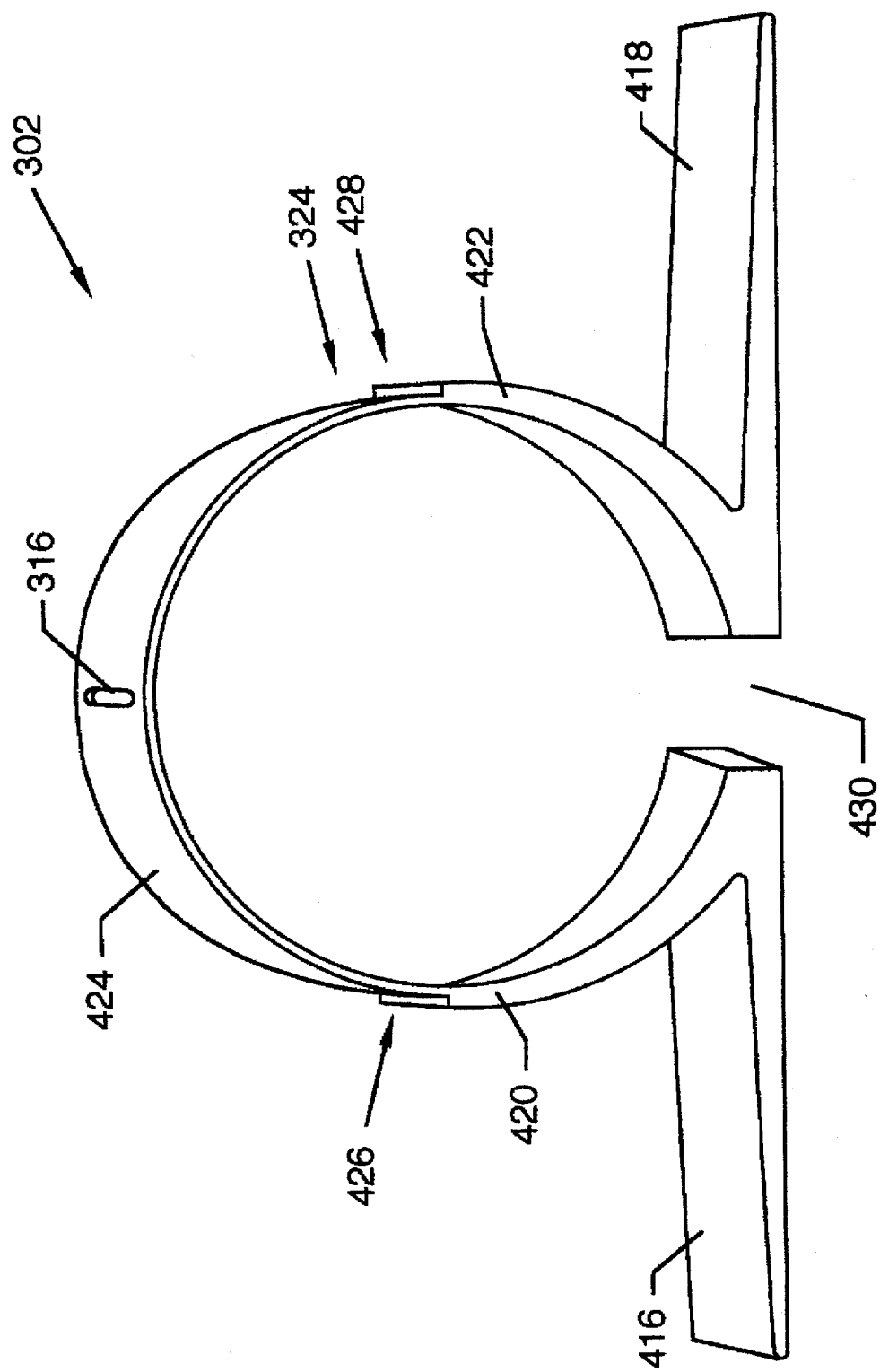
FIG. 23 illustrates an isometric view of a clip.
Figure 24:
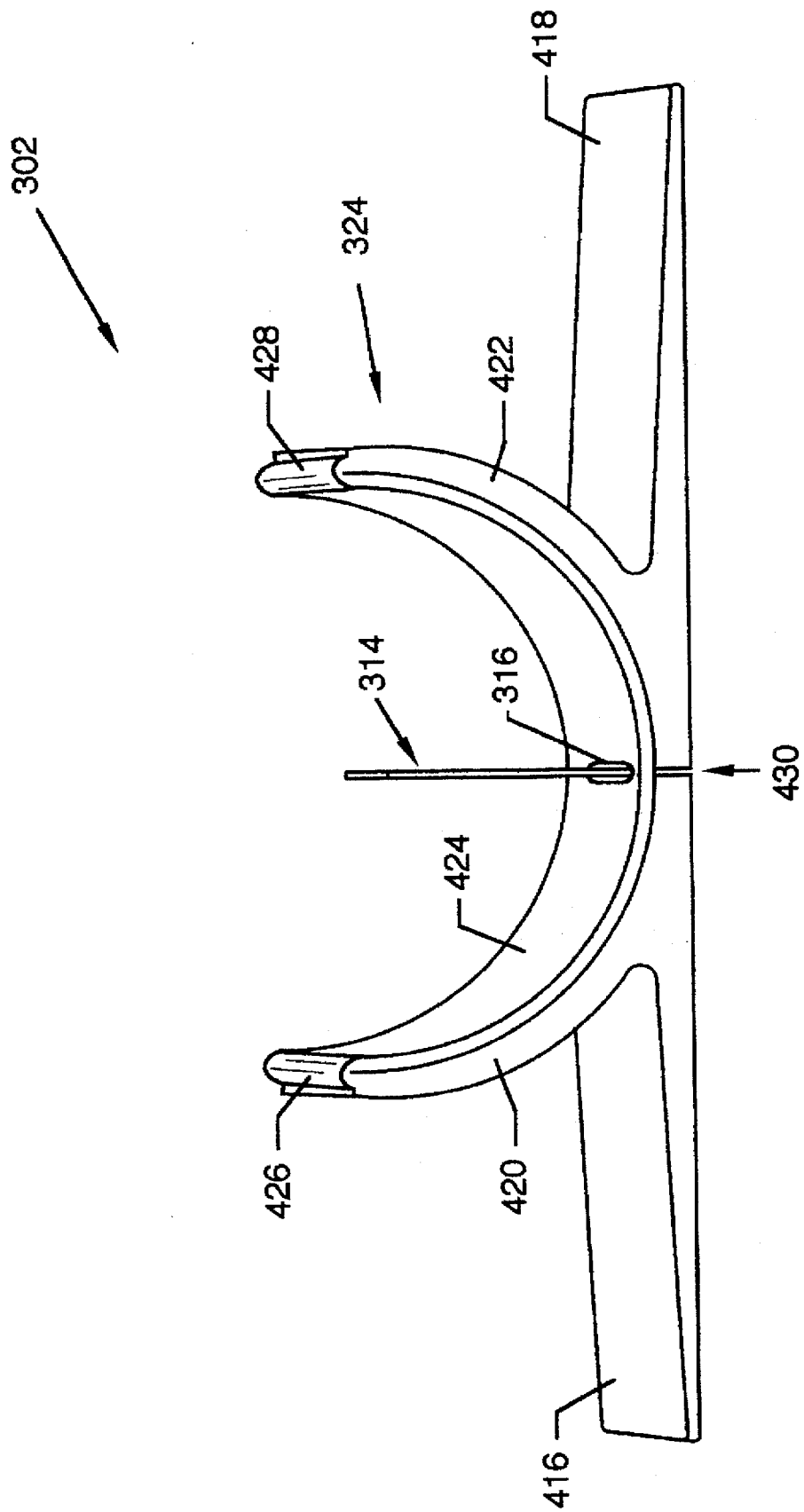
FIG. 24 illustrates an isometric view of a collapsed clip.

FIG. 23 illustrates an isometric view of the clip 302, all numerals corresponding to elements previously described. The flexible clip 302, of one piece integral plastic design, includes opposing tapered and planar base members 416 and 418 supporting the circular portion 324 of the clip 302. The circular portion 324 includes lower arcular members 420 and 422 which are approximately 90 degree arc segments intersecting the base members 416 and 418 respectively. A thin flexible arcular member 424 of approximately 180 degrees arc extends between transition areas 426 and 428 located at the upper region of the arcular members 420 and 422. The lower regions of arcular members 420 and 422 are separated by a variable potential space 430 thus allowing the clip 302 to be flexed as required. The thin arcular member 424 is manufactured and delivered collapsed inwardly as illustrated in FIG. 24 to present a profile receptive of the indwelling tube, line or appliance residing in the securement portion 306 as the dressing membrane portion 308 is flexed at fold line 312 bringing the dressing membrane portion 308 and securement portion 306 into apposition. As delivered to the user a frangible film seals the juncture of the outer margin of thin arcular member 424 with outer margins of members 420, 422 and the outer margins of juncture of clip tapered base members 416, 418 across variable potential space 430.

FIG. 24 illustrates a view of the clip 302 in the low profile position, all numerals corresponding to elements previously described. The base material 304 which is attached to the clip is not shown. Space 430 is opened up to receive tubing, line or appliance by grasping the upper end of the arcular members 420 and 422 between the thumb and index finger as the dressing membrane portion 308 is folded over and on to the tubing, line or appliance and the skin puncture site.

FIG. 25 illustrates the dressing membrane 310 in alignment and attachment to the base material 304 and the base material 304 to clip 302, all numerals corresponding to elements previously described. The base material 304 is fastened such as by gluing or welding to the underside of the tapered base members 416 and 418 at the sides of the variable potential space 430 and to the inner surfaces of the arcular members 420, 422 and 424 as also illustrated in FIG. 26. Adhesive is applied to the interior surface of base material 304 lining the clip 302 in an area conforming to the area of the interior of arcular members 420, 422 and 424 and its opposing surfaces at clip tapered base members 416 and 418 bordering variable potential space 430. Adhesive 435 is applied to the skin contact surface of dressing membrane 310 including the areas directly subjacent to tapered base members 416 and 418, except for adhesive-free portions 397a and 397b. The removable backing strip 314 covers areas of adhesive 435, illustrated in FIG. 26, and is stripped away to reveal in succession the adhesive layer 435 in the area where dressing membrane 310 via the base material 304 secures by glue 434 to the tapered base members 416 and 418, the adhesive 435 on either side of the variable potential space 430 and the adhesive 435 lining the interior surface of base material 304 bonded to arcular structures 420, 422 and 424. The two ends of removable backing strip 314 are applied on either side of slit 316, to the inner adhesive 435 covered surface of base material 304 opposite its area of bonding by glue layer 432 to clip 302. Application or removable backing strip 314 during manufacture continues as removable backing layer 314a in counter-clockwise and clockwise directions on left and right sides of slit 316 respectively to complete backing of the interior of the circular portion of clip 302, sides of the variable potential space 430 and the area of dressing membrane 310 below tapered base members 416 and 418, at the lateral ends of which, the backing doubles back upon itself to retrace its path as removable backing layer 314b and exits the clip 302 via slit 316. The removable backing 314a which comes into initial contact with adhesive 435 has multiple small defects allowing exposure of sufficient areas of adhesive 435 to mutually secure the doubled back portion 314b of the removable backing.

FIG. 26 illustrates a conceptual cross section of clip 302 in attachment to the base material 304, all numerals corresponding to elements previously described. Illustrated in particular are layers including a glue layer 432 on the inside radius of the arcular members 420, 422, and 424, on the areas surrounding variable potential space 430 and on the lower surfaces of the tapered base members 416 and 418. The base material 304 and shroud expansion 322, as illustrated in FIG. 25, secure by the glue layer 432 to the clip 302. The removable backing strip 314 includes a formed tab 436 which is advanced through the slit 316 to strip the backing member 314 from the adhesive band 435 so that adhesive contact can occur, circumferentially securing a tubing, line or appliance to clip 302.

Figure 27:
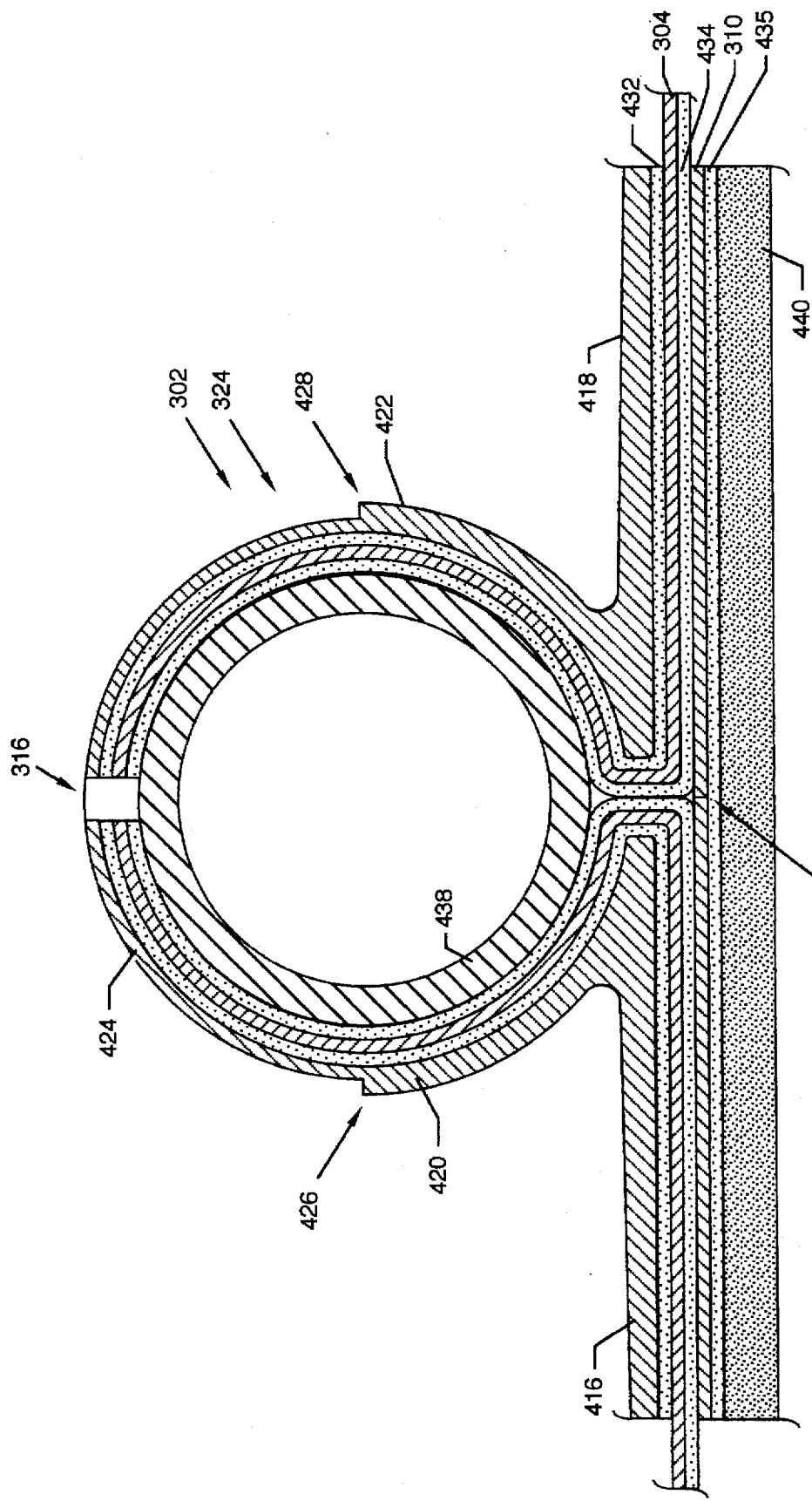
FIG. 27 illustrates a conceptual cross sectional view of the fluid administration tube in adhesive contact with the clip and its associated members.

FIG. 27 illustrates the cross section of a tubing 438 adhesively secured to the clip 302 and clip 302 secured to the epidermis 440, where all numerals correspond to those elements previously described.

The second alternative embodiment, intended to provide an increment in security, would tend to be employed more (but not exclusively) for tubes, lines and appliances of a more critical or of a more long term use nature than the conventional fluid administration line. The former tubes, lines and appliances are apt to be non-linear, and/or inflexible, and/or asymmetrical, and for narrative purposes are referred to as "complex" as opposed to linear, flexible, symmetrical "simple" fluid administration lines. Complex tubes, lines and appliances currently often come in a substantial package. The complex tubes, lines and appliances could be optionally installed within the securement portion of bandage 300 prior to packaging. Multiple configurations of the securement portion 306 of bandage 300 are needed to serve complex and simple lines, tubes and appliances for end user and for manufacturer's installation. FIGS. 20 and 21 depict configuration for end user installation of complex lines, tubes or appliances.

Figure 28:
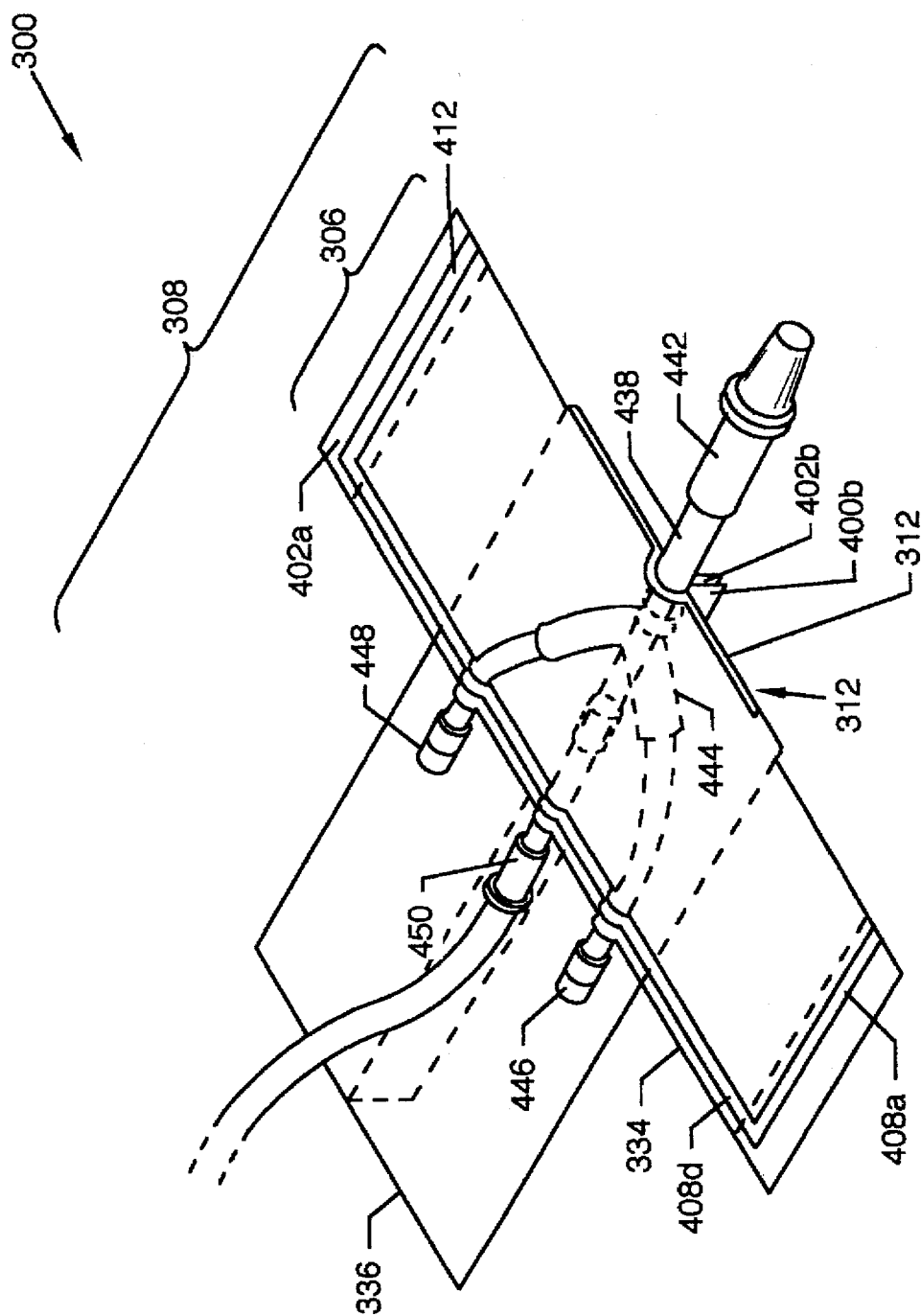
FIG. 28 illustrates the bandage with an incorporated appliance.
Figure 29:
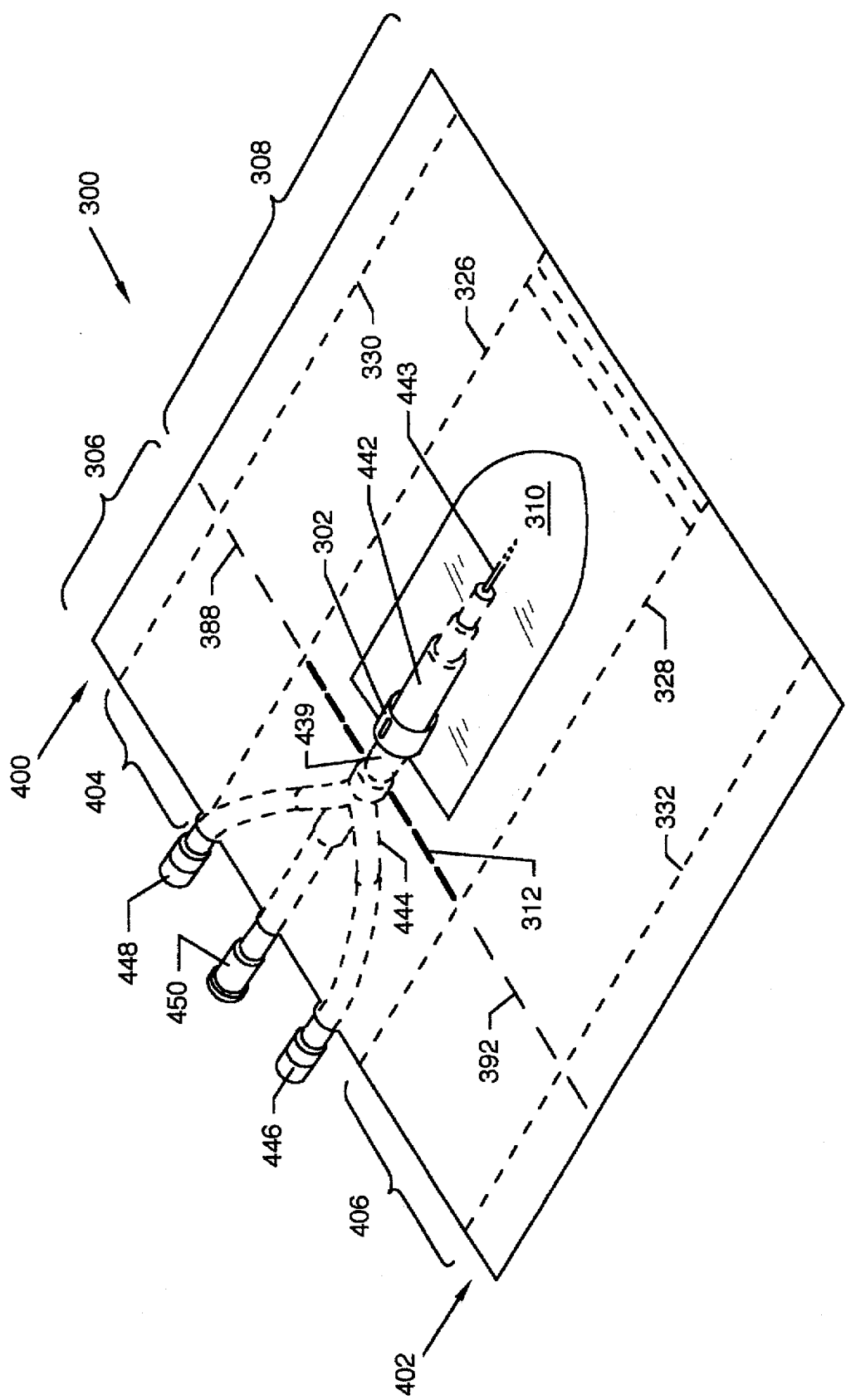
FIG. 29 illustrates an appliance having three ports secured by the bandage of the second alternative embodiment.

As received from the manufacturer for end user installation of tubes, lines or appliances within the securement portion 306, bandage 300 as depicted in FIG. 19 would be manipulated in a fashion analogous to that discussed for bandage 10 relative to FIG. 3. Together with manipulations specific to bandage 300 herein described, this would result in a representative appearance such as in FIG. 29. In advance of attachment to patients, tubes, lines or appliances would be positioned centrally in the space between securement layer backing 305 and base material 304 with suitable extension beyond fold line 312, whereupon securement to the bandage 300 would be effected by removal of backing layer 305 by means of pulling on tab 309. For some tubes, lines or appliances, this securement between layer 307 and base material 304 might occur prior to their packaging, in which case the end user would receive the unit in the stage of deployment depicted in FIG. 28. Further, deployment would continue in steps analogous to those described in conjunction with FIGS. 4, 5, 6 and 7 for bandage 10 and together with manipulations specific to bandage 300 herein described would result in the final use configuration of which FIG. 29 is representative. With bandage 300 inverted from the position depicted in FIG. 28 and with the dressing membrane portion 308 exposed, the dressing membrane portion is rotated about fold line 312 to lie on the skin puncture site. Simultaneously, variable potential space 430 is opened up by grasping the upper ends of arcular members 420 and 422 between the thumb and index finger to encompass the distal end of tubing line or appliance. Firm pressure is then applied with the same thumb and index finger a bit lower on the clip 302 where arcular members 420 and 422 merge into tapered base members 416 and 418 to close clip 302 around the distal end of tubing, line or appliance. As downward pressure is applied to clip tapered base members 416 and 418, the other hand extracts removable backing strip 314 by pulling on tab 436. The peel-away backing 318 is grasped with one hand at the end of planar area 406b nearest fold line 312 and evolves with a counter-clockwise motion as the opposite hand applies counter-traction on the outside of the bandage and presses successively exposed adhesive areas into firm skin contact.

Variations in size, shape, and relative positioning of base material, peel-away backing, removable backing strips, dressing membrane, clip, housing members, adhesive areas, adhesive-free areas, and other elements could be developed without departing from the spirit of the invention. The various pocket or securement portions and dressing membrane portions could be combined to achieve multiple different configurations. For some briefly used tubes, lines or appliances, a dressing membrane may not be needed. An embodiment wherein only a dressing membrane overlies the skin puncture site, dressing membrane being attached reversibly or permanently at its margins to a coinciding defect in the base material is possible. Tourniquets, needles, local anesthetics, alcohol swabs, labels and other equipment useful in the installation of tubes, lines or appliances could be affixed to the outer aspect of any of the embodiments.

Various modifications can be made to the present invention without departing from the apparent scope hereof.

I claim:

1. A bandage for use with a fluid administration line comprising:
   a. a rectangular base of pliable flexible and transparent material forming a bandage, said bandage in general is divided into continuous and adjacent pocket securement and dressing membrane portions, said portions being separated by a fold line;
   b. a transparent dressing membrane intermittently sealed at sealing areas to said rectangular base in a manner to incorporate a plurality of openings between said rectangular base and said transparent dressing membrane, wherein said openings vent an area between said dressing membrane and said rectangular base;
   c. a pocket having an opening aligned along and about said pocket securement portion for capturing a fluid administration line;
   d. an adhesive layer directly applied to said base; and
   e. a peel-away backing over said adhesive.

2. The intravenous bandage of claim 1 wherein:
   said rectangular base is constructed of a polymer material and includes tabs extending upwardly from said base for positioning of the bandage.

3. The intravenous bandage of claim 2, comprising a peel-away backing.

4. The intravenous bandage of claim 2, comprising bridge material.

5. The intravenous bandage of claim 2, comprising a dressing membrane.

6. The intravenous bandage of claim 2, comprising a pocket.

7. The intravenous bandage of claim 2, comprising inner fold line.

8. The intravenous bandage of claim 2, comprising another fold line.

9. The intravenous bandage of claim 2, comprising an adhesive-free area.

10. The intravenous bandage of claim 2, comprising a frangible perforation.

11. The intravenous bandage of claim 2, comprising a tab.

12. The intravenous bandage of claim 2, comprising a planar tab.

13. The intravenous bandage of claim 2, comprising an arrow.

14. The intravenous bandage of claim 2, comprising a rotation arrow.

15. The intravenous bandage of claim 2, comprising a hub in said pocket.

16. The intravenous bandage of claim 2, comprising an intravenous tube in said pocket.

17. The intravenous bandage of claim 2, comprising a fluid administration line in said pocket.

18. The intravenous bandage of claim 2, comprising a pasted edge.

19. The intravenous bandage of claim 2, comprising a seal strip area.

20. A process for pre-attaching and for continuous control of a fluid administration tube to be inserted into a pocket of the bandage of claim 1, comprising:
   a. dividing a rectangular base having an adhesive coating about aligned fold line and frangible perforation lines into a pocket securement portion and a dressing portion;
   b. opening the pocket securement portion including a pocket for capture of a looped portion of a fluid administration tube;
   c. pre-attaching the fluid administration tube within a pocket for continuous control;
   d. connecting the administration tube to a canula hub;
   e. opening the dressing portion and applying it to the skin puncture site of a patient; and
   f. removing the peel away backing from both the dressing and pocket securement portions as successive areas are pressed into adhesive securement with the epidermis, thus anchoring the fluid administration tube and bandage.

21. A process for pre-attaching and for continuous control of a fluid administration tube to be inserted into a pocket of the bandage of claim 1, comprising:
   a. dividing a rectangular base having an adhesive coating about aligned fold line and frangible perforation lines into a pocket securement portion and a dressing portion, said dressing portion including a dressing membrane;
   b. opening the pocket securement portion including a pocket for capture of a looped portion of a intravenous administration tube;
   c. pre-attaching the intravenous administration tube within a pocket for continuous control;
   d. connecting the intravenous administration tube to a canula hub;
   e. opening the dressing portion and applying it to the skin puncture site of a patient; and
   f. removing the peel away backing from both the dressing and pocket securement portions as successive areas are pressed into adhesive securement with the epidermis, thus anchoring the fluid administration tube and bandage.

* * * * *